United States Patent [19]
Gosney, Jr.

[11] Patent Number: 5,658,728
[45] Date of Patent: Aug. 19, 1997

[54] TEMPLATES FOR NUCLEIC ACID MOLECULES

[76] Inventor: William Milton Gosney, Jr., 16 McMillen Rd., Lucas, Tex. 75002

[21] Appl. No.: 197,772

[22] Filed: Jan. 14, 1994

Related U.S. Application Data

[63] Continuation-in-part of Ser. No. 998,008, Dec. 29, 1992, abandoned, which is a continuation-in-part of Ser. No. 717,621, Jun. 19, 1991, abandoned.

[51] Int. Cl.$^6$ .............................. C12Q 1/68; C12M 1/00
[52] U.S. Cl. .............................................. 435/6; 435/287.2
[58] Field of Search .............................. 435/6, 7.1, 7.2, 435/91.1, 287

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.1 |
| 4,728,591 | 3/1988 | Clark et al. | 430/5 |
| 4,941,753 | 7/1990 | Wickramasinghe | 374/120 |
| 5,038,322 | 8/1991 | Van Loenen | 365/114 |
| 5,143,854 | 9/1992 | Pirrung et al. | 436/518 |
| 5,307,311 | 4/1994 | Sliwa, Jr. | 365/174 |

FOREIGN PATENT DOCUMENTS

0385656  9/1990  European Pat. Off. ........ C08F 38/00

OTHER PUBLICATIONS

March, *Advanced Organic Chemistry:Reactions, Mechanisms and Structure*, 1968, McGraw-Hill, New York, pp. 63-65.
Fodor, et al., "Light–directed, spatially addressable parallel chemical synthesis," *Science* 251:767-773 (1991).
McCormick, et al., "A scanning tunneling microscope for biophysical research," *Biophysical Journal* 57:383a (1990).
Blankenship, Bill, "Moving Atoms," *Think* 3:32-33 (1990).
Driscoll, et al., "Atomic–scale imaging of DNA using scanning tunnelling microscopy," *Nature* 346:294-296 (1990).
Dunlap, et al., "Images of single–stranded nucleic acids by scanning tunnelling microscope," *Nature* 342:204-206 (1989).
Barris, et al., "Images of DNA fragments in an aqueous environment by scanning tunneling microscopy," *Biopolymers* 27:1691-1696 (1988).
Foster, et al., "Molecular manipulation using a tunnelling microscope," *Nature* 331:324-326 (1988).
Hansma, et al., "Scanning tunneling microscopy and atomic force microscopy: application to biology and technology," *Science* 242:209-216 (1988).
Lindsay, et al., "Can the scanning tunneling microscopy sequence DNA?", *Genetic Analysis, Techniques, and Applications* 8:8-13 (1991).
Lindsay, et al., "Adsorbate deformation as a contrast mechanism in STM images of biopolymers in an aqueous environment: images of the unstained, hydrated DNA double helix," *Journal of Microscopy* 152:213-220 (1988).

Lindsay, et al., "Imaging deoxyribose nucleic acid molecules on a metal surface under water by scanning tunneling microscopy," *J Vac Sci Technol* 6:544-547 (1988).
Schneir, et al., "Tunneling microscopy, lithography, and surface diffusion on an easily prepared, atomically flat gold surface," *Journal of Applied Physics* 63:717-721 (1988).
Becker, et al., "Atomic–scale surface modifications using a tunnelling microscope," *Nature* 325:419-421 (1987).
Binnig, G., "Paradox in practice: the scanning tunnelling microscope and its applications," *Speculations in Science & Technology* 10:345-352 (1987).
Morawitz, et al., "Multiple image potential effects in a simple model of the scanning tunnelling microscope (STM)," *Surface Science* 180:333-352 (1987).
Silver, et al., "Direct writing of submicron metallic features with a scanning tunneling microscope," *Appl Phys Lett* 51:247-249 (1987).
Staufer, et al., "Nanometer scale structure fabrication with the scanning tunneling microscope," *Appl Phys Lett* 51;244-246 (1987).
Abraham, et al., "Surface Modification with the Scanning tunneling microscope," *IBM J Res Develop* 30:492-499 (1986).
Gomer, R., "Possible mechanisms of atom transfer in scanning tunneling microscopy," *IBM J Res Develop* 30:428-430 (1986).
West, et al., "Chemical applications of scanning tunneling microscopy," *IBM J Res Develop* 30:484-491 (1986).
Pashley, et al., "Scanning tunnelling microscope studies," *Surface Science* 152/153:27-32 (1985) Amsterdam, Netherlands.
"Lawrence Berkeley–Livermore team obtains first direct images of DNA," *Genetic Engineering News*, p. 3 (Mar., 1989).
Yau, et al., "Nanofabrication with a scanning tunneling microscope," *J. Appl Phys* 69:2970-2974 (1991).
Stroscio, et al., "Atomic and molecular manipulation with the scanning tunneling microscope," *Science* 254:1819-1826 (1991).
Whiteman, et al., "Manipulation of adsorbed atoms and creation of new structures on room–temperature surfaces with a scanning tunneling microscope," *Science* 251:1206-1210 (1991).
Lyo, et al., "Field–induced nanometer–to atomic–scale manipulation of silicon surfaces with the STM," *Science* 253:173-176 (1991).
Harbers, et al. "Chemistry of the nucleic acids," *Introduction to Nucleic Acids. Chemistry, Biochemistry and Functions*, Reinhold Bood Corp., New York, pp. 32-57 (1968).

Primary Examiner—James S. Ketter
Attorney, Agent, or Firm—Richards, Medlock & Andrews

[57] ABSTRACT

Templates for the binding and synthesis of biological molecules are disclosed. The templates according to the invention consist of an atomically flat substrate and a three-dimensional pattern formed on the substrate by the positioning of individual atoms or molecules or groups of atoms or molecules to form hillocks. The hillocks are capable of binding to complementary portions of biological molecules or their component molecules.

7 Claims, 13 Drawing Sheets

TEMPLATES FOR NUCLEIC ACID MOLECULES

This is a continuation-in-part of U.S. application Ser. No. 07/998,008 filed Dec. 29, 1992, now abandoned, which is a continuation-in-part of U.S. Ser No. 07/717,621, filed Jun. 19, 1991, now abandoned.

TECHNICAL FIELD OF THE INVENTION

This invention relates to a template for the binding, isolation, and synthesis of biological molecules.

BACKGROUND OF THE INVENTION

Man's quest for understanding about life has inspired scientists to explore more deeply into life's biochemical origins. Entire disciplines have developed around obtaining a better understanding of molecules of biological significance including DNA (deoxyribonucleic acid), RNA (ribonucleic acid), proteins, and their respective component molecules. A project to determine the entire human genome was recently initiated by the National Institutes of Health. The eventual goal is to map and sequence the human genome, as well as the genomes of other organisms widely used in research. With such a map, scientists will be better equipped to pinpoint the causes or contributing factors for disease. Once a cause has been determined, the cures are often not far behind.

For this and other reasons researchers are continually looking for ways to manipulate nucleic acids. New methods and devices which can be used to separate, isolate and detect nucleic acids help to drive advancements in the detection and treatment of genetic disorders. Each new development in the ability to manipulate genetic processes has its own characteristics which researchers can exploit to advance in directions which were not before possible.

Scientists have already determined that numerous diseases are linked to defects in the molecules of biological significance, whether at the genetic level (DNA) or at the point of assembly of the final product molecules (i.e., proteins). If the defect occurs in the genetic material itself, one proposed form of therapy involves treatment through the administration of non-defective genetic material. Recently, the first patient was authorized to receive human gene therapy. The patient has Severe Combined Immunodeficiency Disorder (SCID), which has been traced to a defective gene. The therapy involves the infusion of the patient's own white blood cells, after the cells have been genetically engineered to contain a correct version of the defective gene. A recent report indicated that the infused cells were thriving and the patient was doing well. Aside from the obvious benefits, gene therapy provides other treatment advantages over prior methods for treating SCID. Prior treatment methods confined patients to a completely sealed, sterile environment. (Genetic Technology News, Vol. 11, No. 1, p. 13 (January, 1991)). Additionally, the Food and Drug Administration has given the National Cancer Institute permission to treat fifty patients suffering from metastatic melanoma with genetically engineered immune system cells that specifically home in on tumors. (*Genetic Technology News*, Vol. 11, No. 1, p. 8 (January, (1991)).

As the use of gene therapy increases, so does the demand for properly coded, non-defective genetic material. Current means for DNA synthesis are plagued with some limitations, as well as potential health concerns. One method employs recombinant technology. Essentially, the desired genetic sequence is isolated and inserted into bacterial plasmids via recombinant techniques. As the bacteria reproduce, more copies of the sequence of interest are also made. Bacteria with the proper sequence insertions are then selected through manipulation of antibiotic resistivity. The incorporation of foreign DNA into bacterial plasmids and manipulation of antibiotic resistivity raises some concerns about the development of "super-bugs" which cannot be combatted with currently available treatments and the effect these "bugs" might have if released into the environment. Furthermore, the recombinant DNA process itself is quite laborious and time-consuming for each preparation of a specific DNA sequence.

Another technique disclosed in U.S. Pat. Nos. 4,683,195 and 4,683,202 is said to enable the amplification, detection, and cloning of nucleotide sequences. The technique depends upon the detection of specific nucleic acid sequences in a sample, using an oligonucleotide primer specific for the desired sequence, and then subjecting the primer-bound material to conditions favoring synthesis of a complementary strand. The method is dependent upon the presence of the sequence of interest in the sample. If the sequence is not present, or has been somehow modified, amplification of the desired sequence may not proceed.

A third technique disclosed permits the synthesis of oligonucleotides independent of bacteria and plasmids. However, this technique may place limitations upon the length of the nucleotide sequence which may be ultimately synthesized. The technique utilizes a combination of solid-phase chemistry, photolabile protecting groups, and photolithography, and it is claimed that it can be applied to any solid phase synthesis technique in which light can be used to generate a reactive group. The synthesis occurs perpendicular to a glass substrate. Photomasking techniques are used to selectively expose areas of molecules on the substrate containing photolabile reactive groups. The focus appears to be upon synthesizing a large number of molecules of limited chain length, as opposed to molecules of genomic chain length, and the length of the molecules synthesized is evidently determined by the number of synthesis steps performed. The greatest number of synthesis steps disclosed is about 20, which would result in a sequence of about 20 nucleotides. (See Fodor, et al., "Light-directed, spatially addressable parallel chemical synthesis", *Science* 251:767–773 (1991.)) Since an average-sized gene consists of 1200 base pairs (i.e., 1200 nucleotides on each strand), this technique would require 1200 discreet steps for synthesis of one average-sized gene.

Patients may also suffer adverse consequences when they have inoperative protein molecules, or the complete absence of a particular protein. In such cases, therapy often involves the administration of the operative protein. SCID is an inoperative protein-induced disease and involves a defective enzyme. Protein therapy often precedes gone therapy in time, as it is a prior step in the diagnostic process. First, the cause of a disease may be narrowed down to the failure of a particular protein, or perhaps its absence. Next, the reason for the failure of the protein is determined. Often, this failure can be traced back to a defect in the gene coding for the protein. In the past, genetically engineered microorganisms have been used to produce the operative proteins needed. Examples of such genetically engineered proteins include insulin and Factor VIII. The use of genetically engineered microorganisms presents the same concerns as discussed for the synthesis of DNA using genetically engineered microorganisms—the long-term effects of creating genetically altered "bugs" is simply not known.

Furthermore, the utility of specific, synthesized, DNA sequences does not lie solely in gene therapy. DNA cloning techniques are enjoying widespread application in such diverse fields as identifying crime suspects, identifying fathers in paternity suits, or identifying potential donors for transplants.

Due to the increasing demand for biological molecules, as a result of their extensive application in human therapy and in medical and non-medical analyses, a safer, more efficient method for synthesizing and isolating these molecules is needed.

SUMMARY OF THE INVENTION

This invention relates to a template and a method for binding and synthesizing biological molecules, and/or molecules complementary to the same. No microorganisms are employed and there is essentially no limit upon the size of the molecules which can be synthesized, i.e., DNA molecules of genomic length can be synthesized using the template and method of the invention. Once a template is produced, it functions by selective binding for synthesizing molecules complementary to the template, with the actual synthesis taking only slightly longer than the complementary binding. The method of the invention is rapid, safe, and repeatable.

In one aspect, the invention relates to a template for selectively binding specific biological molecules. The template consists of a substrate which is essentially flat and a three-dimensional pattern formed on the substrate. The pattern consists of a multiplicity of hillocks comprised of atoms or molecules, or groups of atoms or molecules. The hillocks specifically bind to regions on biological molecules complementary to the hillocks.

In another aspect, the invention relates to a template for synthesizing biological molecules. The template consists of a substrate which is essentially flat and a three-dimensional pattern formed on the substrate. The pattern consists of a multiplicity of hillocks formed of atoms or molecules, or groups of atoms or molecules. The hillocks specifically bind to complementary regions on the component molecules of the biological molecule to be synthesized so that the conformation of the bound component molecules facilitates their polymerization into the desired biological molecule.

In another aspect, the invention relates to a template for the synthesis of DNA molecules of essentially unlimited chain length. The template consists of a substrate which is essentially flat and a three-dimensional pattern formed on the substrate. The three-dimensional pattern consists of a multiplicity of hillocks formed of atoms or molecules, or groups of atoms or molecules. The hillocks specifically bind to complementary nucleotides so that the conformation of the bound nucleotides facilitates the polymerization of the nucleotides into a strand of DNA of the specific sequence desired.

In another aspect, the invention relates to a method for synthesizing biological molecules. The method comprises adding a solution containing the component molecules of the desired biological molecule to be synthesized to a template comprising an essentially flat substrate and a three-dimensional pattern formed on the substrate. The three-dimensional pattern consists of a multiplicity of hillocks formed of atoms or molecules, or groups of atoms or molecules. The hillocks specifically bind to complementary regions on component molecules present in the solution in a specific order so that the conformation of the bound component molecules facilitates their polymerization into the desired biological molecule. The bound component molecules are then subjected to conditions favorable to the polymerization of the component molecules into the desired biological molecule.

In another aspect, the invention relates to a method for synthesizing single-stranded DNA. The method comprises adding a solution containing the deoxyribonucleotide-5'-triphosphates of adenine, guanine, cytosine, and thymine to a template comprising an essentially flat substrate and a three-dimensional pattern formed on the substrate. The three-dimensional pattern consists of a multiplicity of hillocks formed of atoms or molecules, or groups of atoms or molecules. The hillocks specifically bind to complementary deoxyribonucleotide-5'-triphosphates in the solution in a specific order so that the conformation of the bound nucleotide triphosphates facilitates the polymerization of a single strand of DNA of the specific sequence desired. The bound nucleotide triphosphates are then subjected to conditions favorable to the polymerization of the nucleotides into a single strand of DNA.

In another aspect, the invention relates to a method for synthesizing double-stranded DNA. The method comprises adding a solution containing an excess of the deoxyribonucleotide-5'-triphosphates of adenine, guanine, cytosine, and thymine to a template comprising an essentially flat substrate and a three-dimensional pattern formed on the substrate. The three-dimensional pattern consists of a multiplicity of hillocks formed of atoms or molecules, or groups of atoms or molecules. The hillocks specifically bind to complementary deoxyribonucleotide-5'-triphosphates in the solution in a specific order so that the conformation of the bound nucleotide triphosphates facilitates the polymerization of the bound nucleotide triphosphates into a single strand of DNA of the sequence desired. The bound nucleotide triphosphates are then subjected to conditions favorable to the polymerization of the nucleotide triphosphates into a single strand of DNA. In one embodiment, the template is heated to temperatures greater than about 85° C. to release the single strand of DNA from the template. The solution is then subsequently cooled to temperatures less than about 85° C. to allow binding to occur between the newly-synthesized DNA strand and the excess deoxyribonucleotide-5'-triphosphates in the solution. The template solution is then subjected to conditions favorable to the polymerization of the complementarily bound deoxyribonucleotide-5'-triphosphates into a double strand of DNA.

In another embodiment, two complementary DNA strands may be synthesized on templates. After synthesis of the complementary single-stranded DNA molecules is complete, the templates are heated to temperatures greater than about 85° C. The neighboring strands are released from their respective templates into the surrounding solution. Upon subsequent cooling of the solution, the complementary strands of DNA bind to one another.

In another aspect, the invention relates to a method for synthesizing molecules, or portions of molecules, which are complementary to biological molecules. The method comprises adding a solution containing component molecules of the desired complementary molecule to be synthesized to a template comprising an essentially flat substrate and a three-dimensional pattern formed on the substrate. The pattern comprises hillocks formed of atoms or molecules, or groups of atoms or molecules, and is dimensioned to facilitate binding between clusters of the hillocks and complementary component molecules in a conformation facilitating polymerization of the bound component molecules into a complementary biological molecule. The bound component molecules are then subjected to conditions favorable to the polymerization of the component molecules into the complementary molecules.

DETAILED DESCRIPTION

Figure 1:
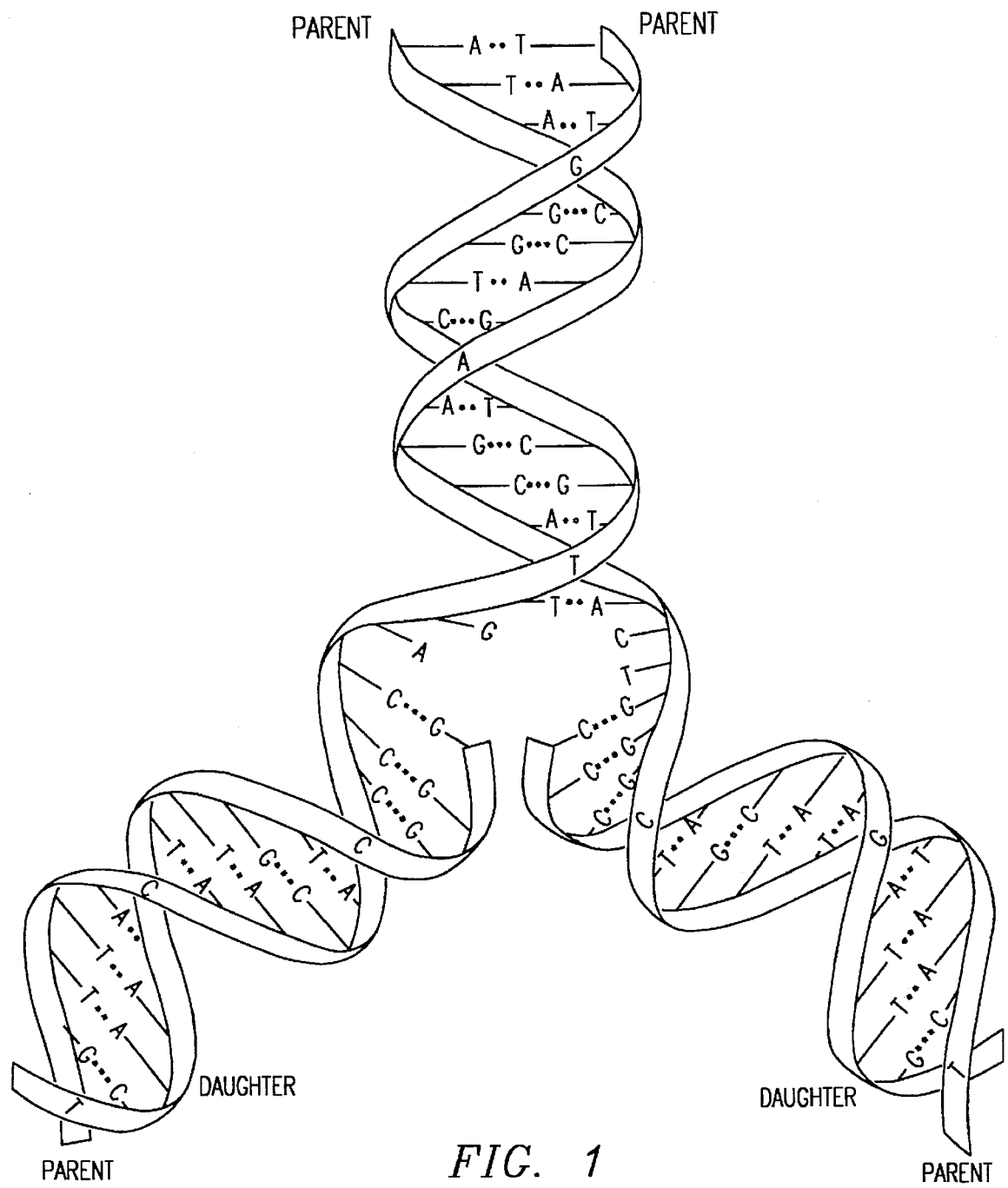
FIG. 1 depicts the replication of the double helix.

A common characteristic of the biological molecules relevant to this invention is that they are synthesized from templates in vivo. These biological molecules include the genetic material (deoxyribonucleic acid or DNA, and, for some microorganisms, ribonucleic acid or RNA), the intermediates in protein synthesis (messenger RNA), and the proteins themselves. This invention relates to the development of templates which can be used to bind or synthesize these molecules in vitro, without the limitations of other in vitro methods discussed previously. No genetically altered microorganisms are generated and sequence length is not limited to lengths which are much shorter than the naturally occurring molecules. Concomitantly, the development of templates for synthesis also facilitates the isolation and purification of complementary molecules, or complementary portions of the molecules.

The following definitions will be applicable:

Biological Molecule

Molecules of import to the reproduction or functioning of organisms, from viruses to humans, and produced from a template in vivo, or capable of complementary binding with a template in vivo or in vitro. Included, without limitation, are DNA, RNA and proteins.

Complementary Binding

Binding exhibited by, for example, the two strands of the DNA double helix and utilized in hybridization techniques for isolating DNA or RNA. Most often, the binding is effected by hydrogen bonds between atoms on complementary portions of each molecule.

Component Molecules

Molecules used to synthesize biological molecules. Included, without limitation, are the ribonucleotide triphosphates and deoxyribonucleotide triphosphates—adenosine triphosphate, cytidine triphosphate, guanosine triphosphate, thymidine triphosphate and uridine triphosphate; the ribonucleotides and deoxyribonucleotides—adenosine, guanosine, thymidine, cytidine and uridine; and the individual nucleotides—adenine, guanine, thymine, cytosine and uracil.

Hillocks

Form the pattern of the templates. "Hillock" refers to an individual atom or molecule, or group of atoms or molecules, positioned on a flat substrate such that a combination of two or more of these hillocks in appropriate three-dimensional conformation is capable of binding either to a complementary component molecule or a complementary portion of a biological molecule. Hillocks can also be formed of molecules, such as the nucleic acid mono-, di-, and tri-phosphates.

Template

Used to refer to a complete series of hillocks on a flat substrate for biological molecules or to a single cluster of hillocks on a flat substrate for individual component molecules.

The templates of the invention comprise a substrate which is selected to enable the formation of small areas on the order of $10^{-2}$ cm$\times 10^{-2}$ cm which are atomically flat. The substrate must be atomically flat to maintain the appropriate distances for base-pair bonding. The height and spacing coordinates of the hillocks ensure the successful complementary binding with the corresponding component molecules or portions of biological molecules. Suitable substrates include gold, nickel, silicon, germanium, highly ordered graphite, carbon or other materials which can be formed atomically flat and which do not interact unfavorably with the organic materials to be applied to the template during DNA synthesis. One method for making flat substrates is discussed in Schneir, et al., "Tunneling lithography, and surface diffusion on an easily prepared, atomically flat gold surface", *J. Appl. Phys.* 63:717–721 (1988).

The binding of molecules to substrates and the utilization of the STM in forming cross-linked organic polymers is known. Ogawa, Kazufumi, EP 0385656, "A Process for the Production of a Highly-Oriented Ultralong Conjugated Polymer," published Sep. 5, 1990 (incorporated herein by reference), discloses the use of the scanning tunneling microscope (STM) to orient the molecules of a monomolecular film in a particular direction for controlled polymerization. Monomolecular films of hydrocarbons having chlorosilyl groups were formed on silicon substrates having an SiO$_2$ film. A bond formed between the silicon of the chlorosilyl group and the SiO$_2$ on the surface, orienting the hydrocarbon in a manner facilitating polymerization. Select unsaturated groups on the film were then linearly inactivated using an equivalent of 5 mJ/cm$^2$ energy from the STM. Subsequent polymerization with radiation resulted in the synthesis of highly-oriented ultralong conjugated polymers. Thus, the STM has been used to facilitate fabrication of ordered polymers. In this invention, binding between hillocks on the surface of the substrate and the biological molecules, as well as the subsequent formation of biological polymers, is contemplated.

The hillocks can be formed of atoms which can be manipulated by the STM. Atoms such as gold, nickel, silicon, germanium, argon, xenon, oxygen, nitrogen, chlorine, fluorine, carbon or hydrogen are suitable candidates. The hillocks can be formed of a single species of atoms or some combination thereof. The hillocks can also be formed using the nucleic acid mono-, di-, or tri-phosphates.

A STM is the device used to make the templates of this invention. It is a very powerful tool for which its inventors won the Nobel prize in physics in 1986. Before and since that time researchers have made great advances in the methodologies used to view and manipulate materials on the atomic level. A STM can be used to very accurately move a bound atom or molecule or group of atoms or molecules to another location, where it remains bound. Compounds, molecules and individual atoms can be moved to and from very precise locations. This can be achieved by various means. Two main ways are the sliding process and the perpendicular process, as described by Stroscio et al., "Atomic and molecular manipulation with the scanning tunneling microscope," *Science* 254:1319–1326 (1991), which is herein incorporated by reference. In the parallel process the tip of the STM is used to slide a bound molecule across a surface to the desired location while the bond between the manipulated atom and the underlying surface is never broken. This method is also used to stack atoms and molecules. Field assisted diffusion is another type of parallel process.

The perpendicular process is that in which an atom, molecule or group of atoms is transferred from the surface to the tip or from the tip to the surface. In all cases the matter to be transferred is an adsorbate and remains adsorbed to the surface. This method can be used to move atoms with impressive accuracy as shown by the removal and replacement of a single silicon atom, shown in FIG. 2D of the Lyo, et al., "Molecular manipulation using a tunneling microscope," *Science* 253:173–176 (1991). Lyo discloses that the STM can be used not only to remove Si atoms, but it can also be used to deposit them anywhere on the surface (See Lyo p. 175, middle column, first full paragraph (discussing FIG. 4 of that article)).

The prior work involving STMs clearly indicates through using such language as adsorbed, bound, or pinned to describe the bonds made by the STM between the adsorbates and the surface that such bonds are strong bonds. Foster et al. disclosed that this bond is the strongest of all bonds, the covalent bond. (Foster, et al., "Molecular manipulation using a tunnelling microscope," *Nature,* 331:4–326 (1988)). More recently, Stroscio disclosed that various types of bonds can be involved. (Stroscio et al., "Atomic and molecular manipulation with the scanning tunneling microscope," *Science,* 254:1319–1326 (1991)).

Whatever bonds are involved, it is evident from the literature that they are strong ones, and researchers have not had problems keeping their adsorbates pinned to a variety of surfaces indefinitely, whether they are in air, vacuum or in a liquid. There is almost never any mention of the adsorbates' stability because for all intents and purposes they are permanent structures. One researcher took 22 hours to spell IBM with xenon atoms (a gas) with no mention of instability of the atoms (Blankenship, B., "Moving atoms," *Think* 3:33–34 (1990)). Adsorbates have ranged in character from complex molecules such as dimethyl phthalate (a liquid) (Foster, et al., *Nature* 331:324–326 (1988)) to simple molecules such as carbon monoxide (a gas) to individual atoms whether they are solids (Si, Pt, Ni) or gases (Xe, Ar, etc.) (Stroscio, A., et al., *Science* 254:1319–1326 (1991); Blankenship, B., *Think* 3:33–34 (1990)). The gases and liquids moved in these references are not harder than gold. In fact, most adsorbates studied to date are not harder than gold, but they are bonded to other elements. Oxygen, nitrogen, fluorine, and chlorine are all gases at standard temperatures and pressure (STP) in their pure elemental state, but they are also all capable of bonding with other elements, creating molecules and compounds which are stable under the most tortuous conditions, much less under the gentle temperatures and buffers used to manipulate nucleic acids. When they are a constituent part of one of these compounds from which the hillocks of this invention will be formed, they are in a position to hydrogen bond just as the oxygen and nitrogen atoms which are part of nucleic acids are able to hydrogen bond.

The coordinates for hillocks made from atoms, or groups of atoms were determined using dimensions obtained from published reports giving measurements by techniques such as x-ray crystallography. Published bond distances and bond angles within individual component molecules and between component molecules (such as by hydrogen bonding) were used to calculate hillock heights and spacings for a cluster of hillocks. Each cluster of hillocks forms a three-dimensional pattern for individual component molecules of biological molecules or complementary regions on the biological molecules. For example, the template for the binding or synthesis of DNA consists of a series of hillocks which together form a pattern representing the strand of DNA complementary to the strand desired to be bound or synthesized. In the case of the binding or synthesizing of RNA, the template consists of a series of hillocks which form a pattern representing the strand of DNA from which the RNA is transcribed.

The binding of nucleic acids to the template will be useful for the isolation and detection of a specific species of DNA or RNA. This technique may be useful in the detection of genetic disorders either in the DNA or RNA. It could be useful for individual identification. The detection of variable numbers of tandem repeats (VNTRs') is one example of this. Once a template is created complimentary to a known VNTR pattern it can be used repeatedly to screen for that individual since the bonding materials used to make the hillocks of this invention are strongly bonded to a relatively unreactive surface. In a system which detects specific nucleic acid sequences, the DNA must undergo certain preparative steps such as releasing it from the cell. The current invention will also require these steps, however it will require little else. No primers, unstable enzymes, complex series of buffers or variable temperature machines will be required. Only simple hybridization and rinsing buffers should be needed. After the specific VNTR is hybridized to the template and the excess noncomplimentary nucleic acids are washed off, any number of known means for the detection of the bound nucleic acid may be used. (Sambrook, et al., *Molecular Cloning, A Laboratory Manual,* 2d ed, Cold Spring Harbor Press (1989) which is incorporated herein by reference.) The possibilities include, but are not limited to: detection with a spectrophotometer at approximately 260 nm for DNA and approximately 280 nm for RNA; ultraviolet-induced fluorescence emitted by ethidium bromide; an antibody detection system; or any other method which will detect nucleic acids. This method does not have to be specific; it only needs to detect the presence of nucleic acids. The present invention has already determined what nucleic acid it is. If there is DNA (in the case of VNTR analysis) present, it is a match. Otherwise there is no match.

For protein synthesis, the hillocks can form a pattern representing the particular messenger RNA from which the protein is translated. Although many proteins have a tertiary structure, the tertiary structure is generally programmed by the primary structure or sequence. Therefore, even globular proteins can be synthesized as they are in vivo—from a template.

The coordinates of the hillocks can be adjusted to reflect more precise bond angle and bond distance measurements that may be possible due to advancements in techniques and instrumentation. It is contemplated that the present method can thus be adapted to making templates for a wide variety of biological molecules.

In a preferred embodiment, the invention relates to a template for the synthesis of DNA molecules. The literature reports that DNA molecules occur in nature in the form of a double helix. During replication, the helix is unwound by certain chemical proteins and each half of the parent double-helix is able to form a complementary half, producing two identical parent-daughter offspring helices identical to the original parent strand. As is well known in the field of genetics, each of the offspring has one strand from the parent, and a newly synthesized strand called a daughter. During cell division, each new cell takes one set of identical DNA molecules. The backbones of the helices essentially comprise a chain of phosphate-sugar molecules covalently bound to one another.

The essence of the genetic code is found in the sequence of the nucleotide bases which connect the two helices together by base-pairing. The nucleotide bases which connect the two strands of the DNA double helix are adenine, cytosine, quanine, and thymine. The type-B double-strand DNA molecule originally described by Watson and Crick is about 20 Angstroms (Å) in diameter. The double helix makes a complete rotation about the center axis every 34 Å. Ten nucleotide base pairs occur every rotation of the helix; hence, each nucleotide base pair is separated from adjacent nucleotide base pairs by about 3.4 Å on the center axis. Each base pair lies essentially in a plane roughly perpendicular to the center axis.

The two nucleotide bases which form each base pair are very specific in their ability to bond to one another. For example, adenine forms two hydrogen bonds with thymine, and cytosine forms three hydrogen bonds with guanine. Crystallographic X-ray analysis of these nucleotide base pairs has disclosed details of the structure indicating that the pairing of the molecules is very specific. Although hydrogen bonding is electrostatic and is not as strong as covalent bonding, it is sufficiently strong to ensure the specific bonding of each base to its proper complementary partner in the proper orientation. The invention is also directed to binding nucleic acids by overall charge. DNA and RNA molecules have a charge which varies due to several factors, for example, pH and ionic concentration. The hillocks of the substrate can be given a slight opposite charge to the DNA, not enough to cause an overwhelming attraction but enough to lightly attract the nucleic acid molecule. Under these conditions the DNA or RNA may line up on the hillocks due to stearic constraints. This method may also be useful to bind charged proteins with specific tertiary and quarternary configurations.

During replication, when the two strands of the double helix separate, each nucleotide base is able to attract only its proper complementary partner in forming the newly synthesized daughter strand. Hence, adenine in the parent strand attracts thymine in the complementary daughter; thymine attracts adenine; guanine attracts cytosine; and cytosine, guanine.

FIG. 1 depicts the replication of the double helix. As two parent strands unwind, each nucleotide base binds with its complementary partner available in the surrounding environment to synthesize a daughter strand identical to the opposing parent strand. As a result, the original double helix is able to replicate itself.

Figure 2:
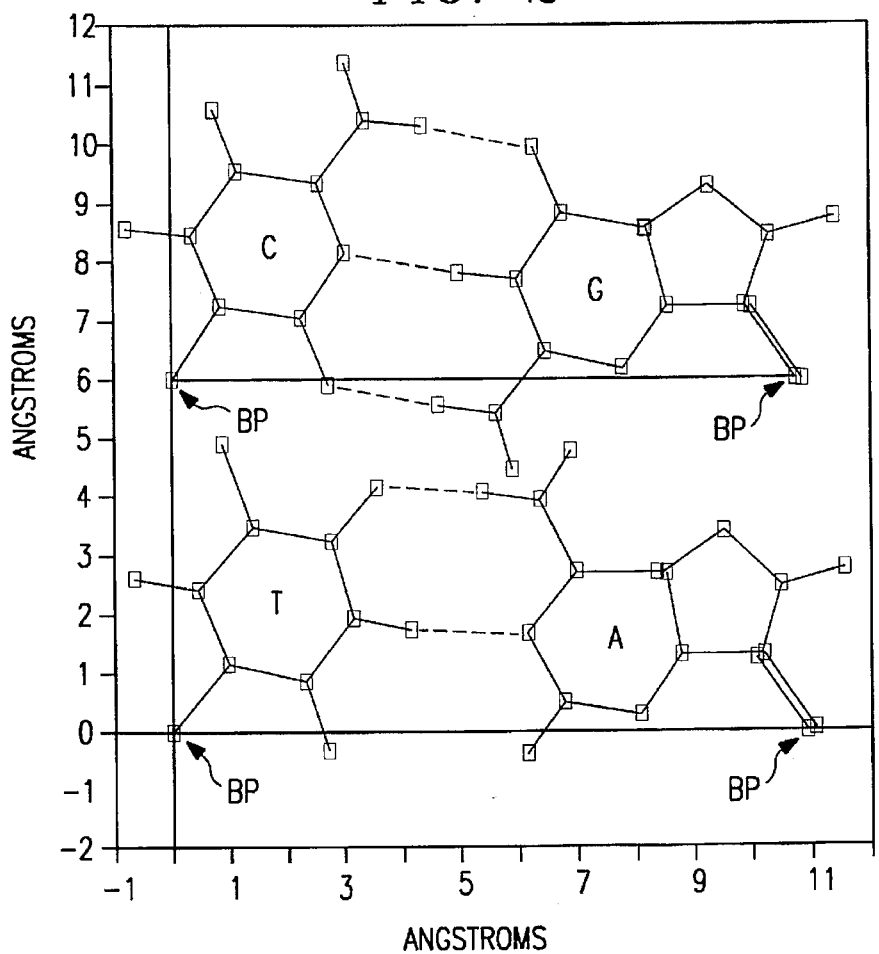
FIG. 2 depicts the detailed configuration of the hydrogen-bonded base pairs interconnecting the two phosphate-sugar backbones: adenine-thymine and guanine-cytosine, wherein BP=chain bond points to the phosphate-sugar backbone.

FIG. 2 depicts the detailed configuration of the hydrogen-bonded base pairs interconnecting the two phosphate-sugar backbones. The plots were made from computer-generated coordinates for the DNA base pairs. The bond points (BP) to the phosphorus-sugar chains are shown. The coordinate points of each atom are critical to determine the template hillock heights and spacings. The dotted lines represent the hydrogen bonds. FIG. 2 is based upon the dimensions and spacings derived from x-ray crystallography studies of purines and pyrimidines. (See *The Nature of the Chemical Bond*, Linus Pauling; *Chemistry for the Modern Mind*, Joachim Rudolph). Using this data, the chain-to-chain hydrogen bond spacing was calculated to be:

Adenine-thymine: 10.92Å

Guanine-cytosine: 10.69Å

The dimensions originally published by Watson and Crick for type-B DNA represent average dimensions. The actual dimensions can vary slightly with the local nucleotide sequences.

The template heights can be adjusted to provide for a perfect alignment of the molecules comprising the phosphate-sugar backbone; or they can be based on the average spacing, which causes a slight variation in the phosphate-sugar chain bond-point centerline. Although the computations here provide a straight phosphate-sugar backbone bond-point centerline, the small variation that would result from using average spacing in the hillock dimensions is not expected to be of major significance in that the variation is likely smaller than the accuracy of placement of the template atoms.

EXAMPLE 1

Selective Binding

In one embodiment, the template, prepared as described in Example 2 below, can be used to selectively bind and, thereby, isolate or purify complementary DNA strands or complementary RNA strands such as messenger RNA (mRNA). One template can contain several or more copies of sequence patterns complementary to the biological molecule of interest.

Since proteins are translated from mRNA in Vivo, and mRNA is transcribed from DNA, a template containing hillock patterns resembling the complementary portion of the DNA coding for a particular mRNA can be prepared. The template can then be used to isolate the desired mRNA from biological samples under conditions favorable to hybridization between the mRNA and the template—for example, lower temperatures. The specific mRNA will bind to the template and the non-specific mRNAs and other molecules can be removed in a washing step. Subsequently heating the template would then facilitate the removal of the specific mRNA from the template for further application and use.

EXAMPLE 2

Formation of the Template

Figures 3A, 3B:
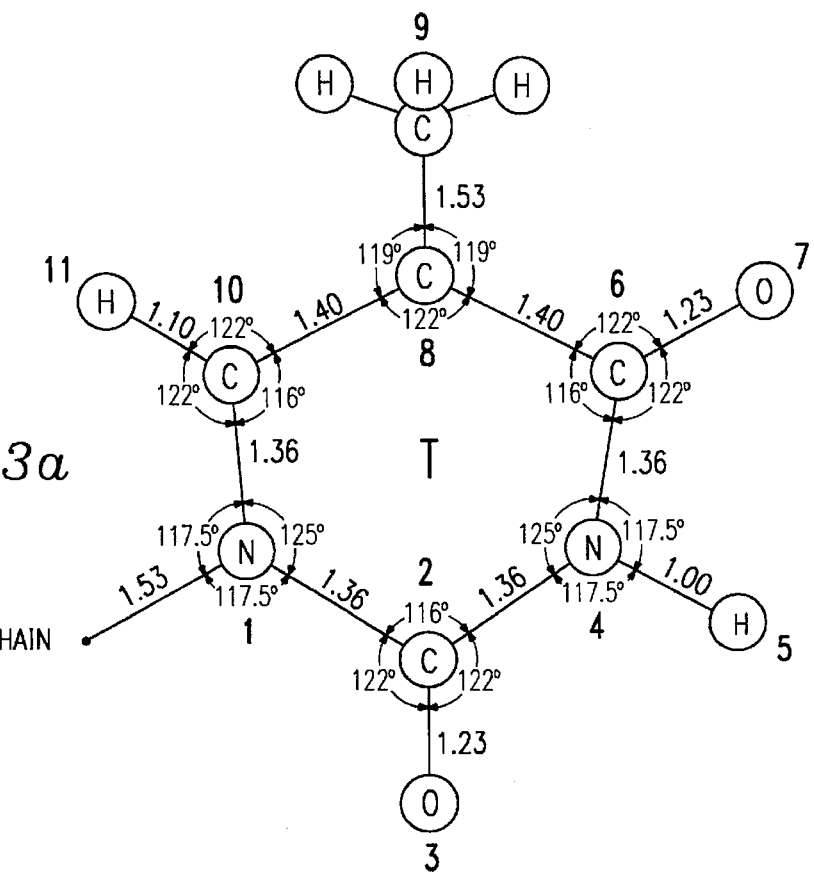
FIG. 3a depicts the detailed structure of thymine based upon X-ray crystallographic analysis.
FIGS. 3b, 3c and 3d depict the detailed structures of cytosine, adenine and guanine, respectively.
Figure 3C:
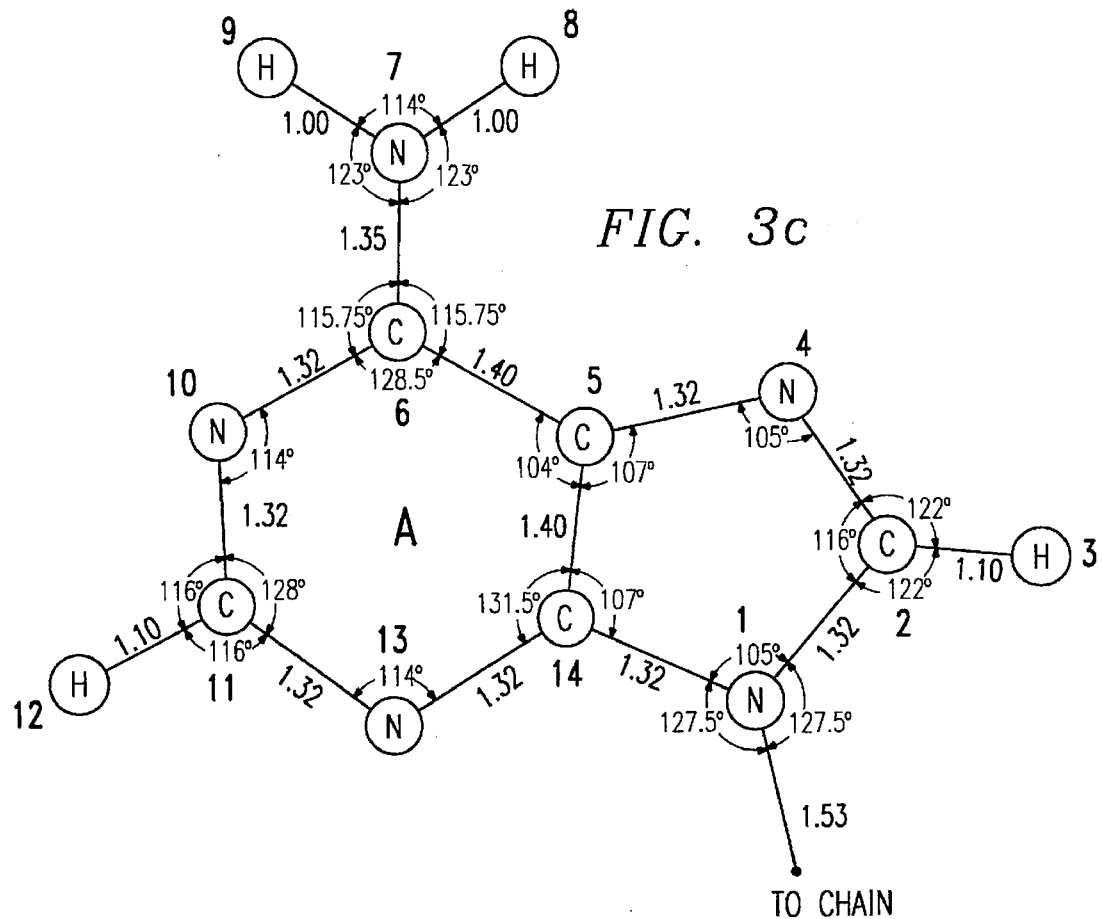
Figure 3D:
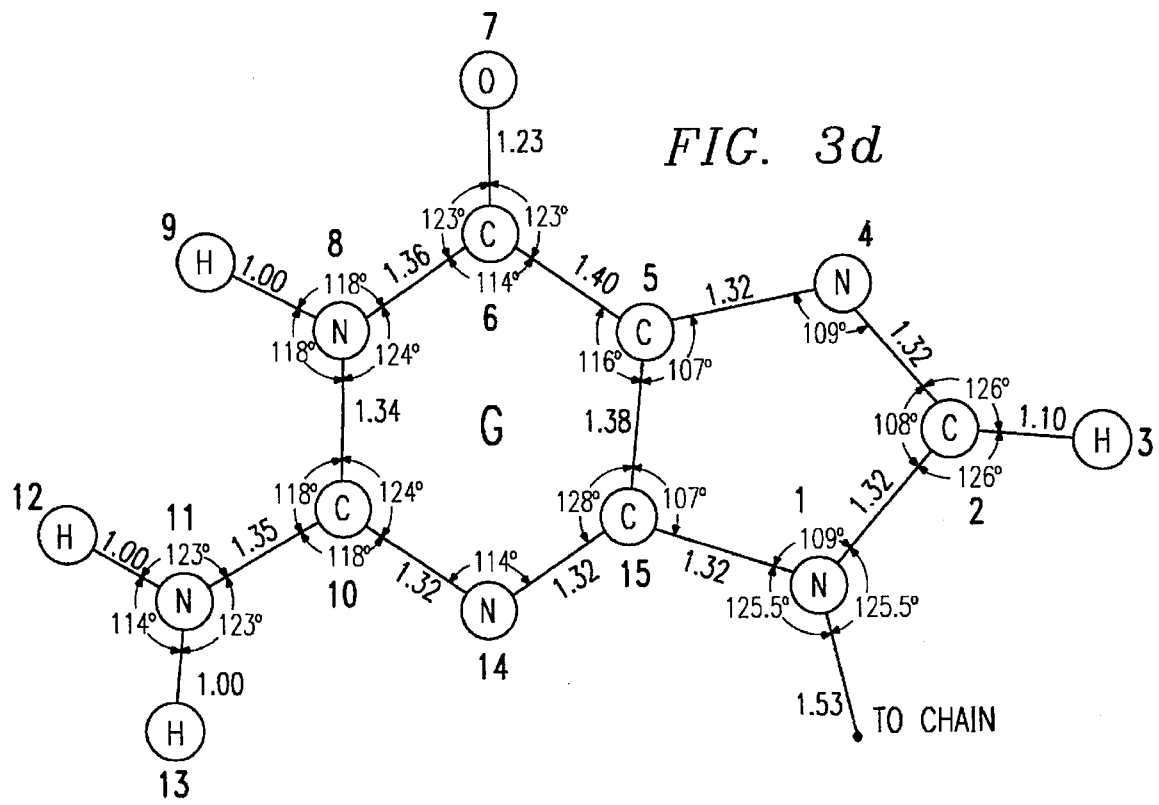

FIGS. 3a, b, c, and d show the detailed atomic dimensional data for each nucleotide base as listed in Pauling, supra, based on X-ray analysis of bulk crystalline samples.

This data was used to calculate the X and Y coordinates for the hillocks. Small errors of closure were discovered in the data—the most significant being 0.103 Å in adenine— which likely are caused by rounding the measured data. This error of closure in the published data can be seen as a slight double figure in the computer plot of FIG. 2 for adenine and guanine. It is not expected that this error of closure will introduce any significant error into the computations of the template structures.

Figure 4A:
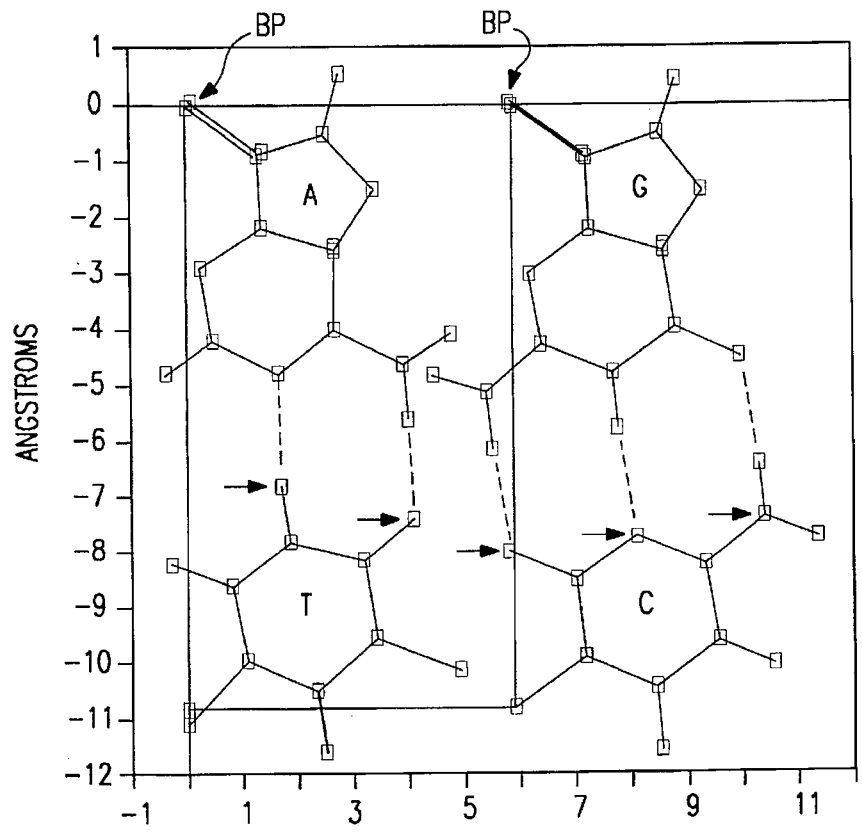
FIG. 4a depicts the detailed configuration of the nucleotides adenine and guanine with respect to common phosphate-sugar bond-points as shown at the upper left of each base, wherein BP=chain bond points to the phosphate-sugar backbone.
Figure 4B:
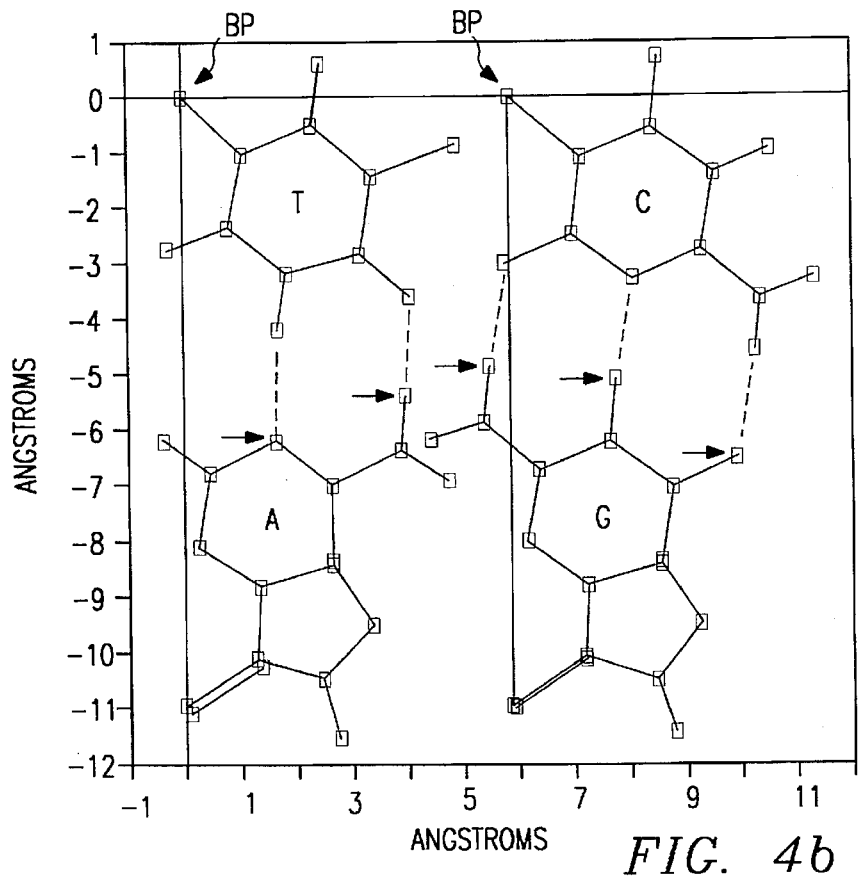
FIG. 4b depicts the detailed configuration of the nucleotides thymine and cytosine with respect to common phosphate-sugar bond-points as shown at the upper left of each base, wherein BP=chain bond points to the phosphate-sugar backbone.

FIGS. 4a and 4b depict the detailed configuration of the structure of each nucleotide with respect to a common phosphate-sugar bond-point. These sketches were made by computing the coordinates of each of the atoms using the dimensional data presented in FIGS. 3a–d and performing appropriate rotation and inversion so that each of the four nucleotides has the same orientation and starting origin. Thus, FIG. 4a shows adenine and guanine with the phosphate-sugar bond-point (BP) to the upper left; FIG. 4b shows thymine and cytosine with the phosphate-sugar bond-point (BP) to the upper left. The phosphate-sugar chain bond-point is indicated by a "0" on the Y axis in FIGS. 4a and 4b. The dotted lines represent the hydrogen bonds. Since the radius of the effective center of the DNA chain is approximately 9.1 Å, the distance on the Y axis (in these FIGURES) from the atoms involved in the hydrogen bonding (marked by arrows in the FIGURES and which correspond to the template hillocks) to a point 9.1 Å below the phosphate-sugar chain bond-point was measured and was used to calculate the preferred height coordinate for each hillock. These coordinates are presented in the "Template Height H" column in Table I below.

TABLE I

TEMPLATE TOP POSITION SUMMARY
(CHAIN TO CHAIN DIRECTION IS VERTICAL)

| Nucleotide | Atom* | R | Z | Chain Height C | Angle | X | Y | Template Height H | Atom in Template Complement |
| --- | --- | --- | --- | --- | --- | --- | --- | --- | --- |
| Thymine | 5H | 1.6954 | −6.1496 | 9.1000 | 31.02 | 0.9736 | 1.4530 | 2.9504 | N |
|  | 7O | 4.0666 | −5.3804 | 9.1000 | 31.02 | 2.0955 | 3.4952 | 3.7196 | H |
| Adenine | 10N | 1.7512 | −6.7805 | 9.1000 | 31.02 | 0.9024 | 1.5008 | 2.3195 | H |
|  | 9H | 4.1672 | −7.3334 | 9.1000 | 31.02 | 2.1473 | 3.5714 | 1.7666 | O |
| Cytosine | 3O | −0.4335 | −4.6293 | 9.1000 | 31.02 | −0.2234 | −0.3715 | 4.4707 | H |
|  | 4N | 1.8251 | −4.9971 | 9.1000 | 31.02 | 0.9405 | 1.5642 | 4.1029 | H |
|  | 7H | 3.9781 | −6.2753 | 9.1000 | 31.02 | 2.0499 | 3.4093 | 2.8247 | O |

TABLE I-continued

TEMPLATE TOP POSITION SUMMARY
(CHAIN TO CHAIN DIRECTION IS VERTICAL)

| Nucleotide | Atom* | R | Z | Chain Height C | Angle | X | Y | Template Height H | Atom in Template Complement |
|---|---|---|---|---|---|---|---|---|---|
| Guanine | 12H | −0.0602 | −7.9602 | 9.1000 | 31.02 | −0.0310 | −0.0516 | 1.1398 | O |
|  | 9H | 2.1422 | −7.6344 | 9.1000 | 31.02 | 1.1039 | 1.8359 | 1.4656 | N |
|  | 7O | 4.3260 | −6.3186 | 9.1000 | 31.02 | 2.2291 | 3.7074 | 2.7814 | H |

*Prefix numbers refer to numbers in FIGS. 3a–d.
Column Legend:

| | |
|---|---|
| Nucleotide: | Name of nucleotide |
| Atom: | Atom type in the atomic bonds. Number refers to numbers in FIGS. 3a–d. |
| R: | Horizontal displacement of hillock along the nucleotide centerline relative to centerline of phosphate-sugar backbone in angstroms. [FIXED] |
| Z: | Coordinate of hillock height relative to phosphate-sugar backbone in angstroms. [FIXED] |
| Chain Height C: | Designates height of phosphate-sugar backbone above template surface in angstroms. This is somewhat arbitrary - 9.1 Å is a reasonable value. See text. |
| Angle: θ | The angle between nucleotide template C/L (centerline) and the phosphate-sugar backbone C/L in degrees.⁺ |
| X: | Coordinate of template hillock in the template plane relative to the intersection of the template centerline and the nucleotide centerline in angstroms. $X = R \cos \theta$. |
| Y: | Coordinate of template hillock in the template plane relative to the intersection of the template centerline and the nucleotide centerline in angstroms. $Y = R \sin \theta$. |
| Template Height H: | Height of template hillock relative to template plane in angstroms. [This computation changes with chain height.] $H = C - Z$ |
| Atom in template complement: | Atom in complementary nucleotide bond site or possibly the template bond site. |

⁺Representing the angle between the planes of the nucleotides and the phosphate sugar chain.

The first column in Table I provides the name of the nucleotide. The second column lists an arbitrary identification number assigned to the atom type as seen in FIGS. 3a–3d, along with the atom type, for the atoms which are involved in the hydrogen bonding between complementary molecules. The third code, labelled "R", represents the horizontal distance from the centerline of the phosphate-sugar backbone to the hillock. The fourth column, labelled "Z", represents the vertical distance of the hillock from an imaginary centerline drawn above the surface of the template representing the phosphate-sugar backbone. If the sugar backbone coordinates are (0,0), then the next column "Z" is the distance in angstroms to the next bonding atom below the phosphate-sugar bond-point. Thus, "R" and "Z" represent the relative coordinates in angstroms from the phosphate-sugar bond-point for each of the hydrogen bonds on each of the nucleotides.

However, since it is more convenient to choose the surface of the template as the height coordinate Z=0, one can then somewhat arbitrarily choose the height of the chain bond-points above the template surface. The height must be selected such that all template hillocks are positive with respect to the surface, and the minimum hillock is one atom. There is no specified maximum chain bond-point height. However, higher chain bond-point heights above the template floor will require higher hillocks which will take longer to fabricate, and which could become fragile, unstable, or unwieldy. Thus, lower chain bond-point heights are preferable.

A chain bond-point height of 9.1 Å represents the estimated radius of a DNA molecule measured at the chain bond-points. The ninth column in Table I, labeled "Template Height", contains the heights, in angstroms, for each of the hillocks for each hydrogen bond of the four nucleotides relative to the 9.1 Å chain bond-point height. A slight change in the chain bond-point height would result in a change in the template height since the chain bond-point to template height distance is invariant. (The chain bond-point to template height is depicted in column Z in Table I above.) However, this slight adjustment of chain bond-point height is within the scope of this invention.

Figure 5:
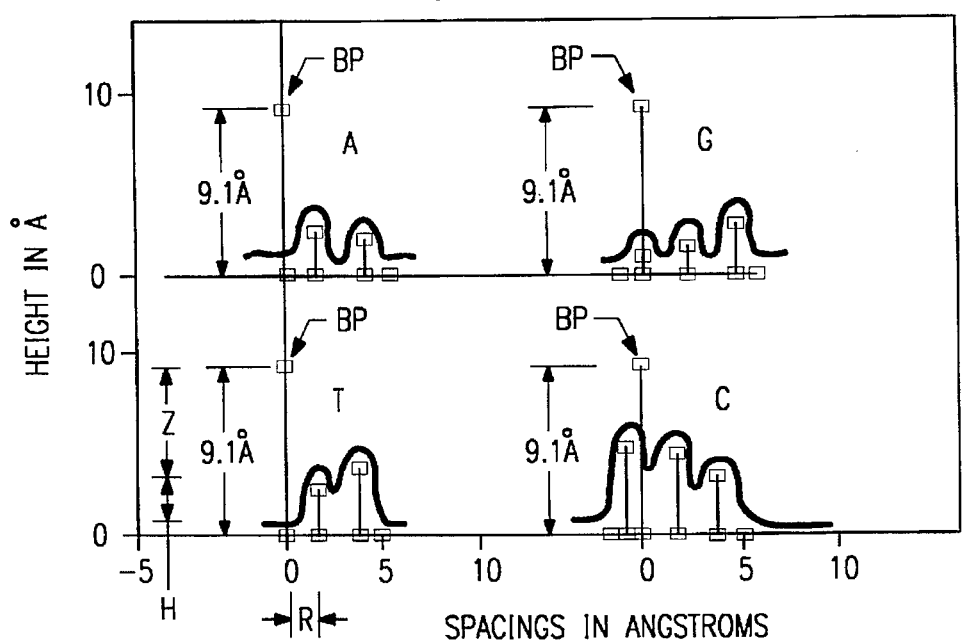
FIG. 5 depicts the preferred spacings and heights of the template hillock structures for each nucleotide relative to a phosphate-sugar chain bond-point wherein BP=chain bond points to the phosphate-sugar backbone located 9.1 Å above the template plane and H=template height.

FIG. 5 depicts the preferred spacings and heights of template structures for each nucleotide relative to a phosphate-sugar chain bond-point located 9.1 Å above the crystalline template plane. The template for each nucleotide is comprised of two or more hillocks. The bases of the hillocks can be merged, and the group of two or three hillocks can be formed by a single molecule. These hillock structures represent the coordinate locations of the next atom in the complementary nucleotide. The location of the attachment point of the nucleotide to the phosphate-sugar backbone is also indicated.

The template can be fabricated utilizing a modified scanning tunneling microscope (STM) to form hillocks on a planar substrate. It was recently disclosed that the STM can be used to move individual atoms to form patterns. (Blankenship, B., "Moving Atoms", *Think*, Vol. 3, pp. 32–33 (1990)). The Think article disclosed the spelling of the word "IBM" with xenon atoms using the STM. The STM can be used to position atoms or molecules to form the templates relevant to this invention. In a preferred embodiment, gold or silicon can be used as the substrate material.

The hillocks are formed by operation of the STM in a hillock-synthesis mode (i.e., deposition mode). In a preferred embodiment, the STM forms the hillocks so that the center of the top atom in each hillock is located at the appropriate distance from the intended phosphate-sugar bond-point as denoted by the "R" and "Z" computations in Table I. Assuming that the height of the phosphate-sugar bond-point is 9.1 Å, the heights and horizontal spacings of the hillocks for each nucleotide relative to a centerline on the template surface below the phosphate-sugar bond-points are listed as "Template Height" ("H") and "R" in Table I and illustrated in FIG. 5. Thus, the STM will fabricate small hillocks whose topmost atoms coordinate points are located per the "R" and "Template Height" ("H") listing in Table I in terms of the horizontal and vertical distances, respectively, from the phosphate-sugar backbone centerline. The "X" and "Y" columns represent the corresponding X and Y coordinates for each hillock on the template plane relative to the origin for each nucleotide.

The hillock structures can be made by the formation of mounds on the substrate surface using the STM. The mound heights required are the same as the "Template Height H" listed in Table I. The use of the STM to form mounds on various substrates is known. The deposition of silicon (Si) atoms onto a silicon surface is described in Lyo and Avouris, "Field-Induced Nanometer-to-Atomic-Scale Manipulation of Silicon Surfaces with the STM", *Science*, Vol. 253, pp. 173–176, Jul. 12, 1991 (incorporated herein by reference). The Lyo and Avouris reference discusses the transfer of clusters of up to tens of silicon atoms from the surface to the tip and then the redeposition of these clusters at specific sites on the surface. By using a sequence of pulses of +3 V, silicon clusters were formed and removed from the substrate surface, respectively. The tip was then moved to another location and, by application of a pulse of −3 V, the cluster was redeposited onto the substrate surface at a separate location. The desorption of the Si clusters from the tip was very reproducible. The deposition of germanium atoms is described in Becker et al., "Atomic-Scale Surface Modifications Using a Tunnelling Microscope," *Nature*, Vol. 325, pp. 419–422 (Jan. 29, 1987), (incorporated herein by reference). Becker et al. describes the formation of a "protrusion" on the germanium surface using a tip to surface bias of −4.0 V. Contrastingly, the bias voltage used for taking tunnelling topographs, i.e., scanning the surface, was −1.0 V. In Silver et al., "Direct Writing of Submicron Metallic Features With a Scanning Tunneling Microscope," *Appl. Phys. Lett.*, Vol. 51, No. 4, pp. 247–249 (Jul. 27, 1987), the deposition of dimethyl cadmium is described. The Silver et al. reference is incorporated herein by reference. Silver et al. further reported that the deposit height increased with the time of application of voltage. Deposits were obtained by bringing the tip toward the sample with a voltage of 1–5 V.

In Whitman, et al., "Manipulation of Adsorbed Atoms and Creation of New Structures on Room-Temperature Surfaces With a Scanning Tunneling Microscope," *Science*, Vol. 251, pp. 1206–1210 (Mar. 8, 1991), the construction of piles of cesium atoms is disclosed. (Whitman, et al., incorporated herein by reference.) The pile was created using a bias voltage of +3 V. In Yau, et al., "Nanofabrication with a Scanning Tunneling Microscope," *J. Appl. Phys*, Vol. 69, No. 5, pp. 2970–2974 (Mar. 1, 1991), depositions having angstrom dimensions are described. Yau, et al. discloses that, even using the same voltage pulse, smaller deposits are obtained with shorter pulsing times. In the presence of trimethylaluminum on a graphite surface, a 4 V pulse for 3s resulted in a deposit having dimensions of 40×40×10 nm³. Contrastingly, pulsing with 4 V for 0.2 seconds resulted in a two-component deposit, each component having dimensions of 4×5×2.4 Å with an interspacing of 1.8 Å. (The Yau, et al. reference is incorporated herein by reference.) As is evident from the above, the precise bias voltage to be used is dependent upon the equipment, materials used, and conditions, but is ascertainable.

What is required in the formation of the hillocks is that the positions of the topmost atoms, relative to one another, be as set forth in Table I to participate successfully in hydrogen bonding with the appropriate component molecules. Because of the close spacing of the hillock tops, merging of the bases is acceptable. To achieve these heights, a combination of depositions and depressions made with the STM is also contemplated. Use of the STM in making depressions is also described in the Lyo and Avouris reference. Using the same voltage pulse for mound formation, but shorter tip-sample distances, a mound-in-moat structure was formed. Repeating the pulse resulted in the adsorption of the mound to the tip, leaving behind a hole. FIG. 4 of the Lyo and Avouris reference depicts the depth of the resulting hole as approximately 3 Å. In Yau, et al., higher tip biasing voltages resulted in the formation of holes on the graphite surface. A 5 V pulse for 0.2 seconds formed a hole approximately 30 Å deep (peak to valley).

In a preferred embodiment, a single atomic species can be utilized for all hillock structures and the STM can form the single-species hillocks as close as possible to the preferred heights and spacings. It may be necessary to vary the topmost atom or atoms in each hillock to correspond to the equivalent atom in the nucleotide for which the template is substituting during the DNA synthesis operation. The last column in Table I lists the complementary atom for each bond-point of the four nucleotide templates. Alternatively, the nucleic acids themselves, or their mono-, di-, or triphosphates, can be pinned to the surface to be used as the hillock structures.

In Foster, et al., "Molecular Manipulation Using a Tunnelling Microscope," *Nature*, vol. 331, No. 28, Jan. 28, 1988 (incorporated herein by reference), use of the STM to selectively "pin" molecules to a substrate surface is described. A 3.7 V pulse for 100-ns resulted in the "pinning" of a di(2-ethylhexyl)phthalate molecule to a graphite surface. Foster et al. further discloses that subsequent pulses of 3.7 V could result in the partial erasure of an already pinned dimethyl phthalate molecule. In Lindsay, et al., "Adsorbate Deformation as a Contrast Mechanism in STM Images of Biopolymers in an Aqueous Environment: Images of the Unstained Hydrated DNA Double Helix," *Journal of Microscopy*, Vol. 152, pt. 1, pp. 213–220 (October 1988) (incorporated herein by reference), conditions for pinning DNA molecules to a gold substrate are disclosed. Specifically, DNA was dissolved in 20 nM tris (hydroxymethyl)-aminomethane, 10 mM $CH_3COONa$ buffer (adjusted to pH 7.5 with HCl) to a concentration of a few tens of µg/ml. The plating electrode was biased at −2 V for 2–3 minutes for the deposition of the DNA, which was verified by subsequently operating the STM in the scanning mode. In Dunlap, et al., "Images of Single-Stranded Nucleic Acids by Scanning Tunnelling Microscopy," *Nature, Vol.* 342, pp. 204–206 (Nov. 9, 1989) (incorporated herein by reference), the deposition of poly(dA) on highly oriented pyrolytic graphite (HOPG) is described. One µl of 2.2 µg/µl of poly(dA) in 10 mM Tris, 1 mM EDTA at pH 8.0, 23° C., was placed on a chip of HOPG. The chip was surrounded by a reservoir of water and both were covered for one hour. 0.5 µl of ethanol was added and the droplet was allowed to evaporate. Rinsing was performed by floating the chip on double-distilled water and residual liquid was removed by touching the edge with a tissue. Under these conditions, the bases bound flat to the surface and the sugar moieties were perpendicular. It is contemplated that altered conditions, and the use of the individual nucleic acids or their phosphate derivatives, can result in binding of the nucleic acids in proper orientation to participate in hydrogen bonding for DNA synthesis.

Fabrication of the template can be performed under vacuum and at low temperatures to stabilize the surface and minimize contamination during the fabrication steps. Once formed, the template is maintained at cryogenic temperatures for storage prior to use. The template is then warmed up to room temperature for use.

Figure 6A:
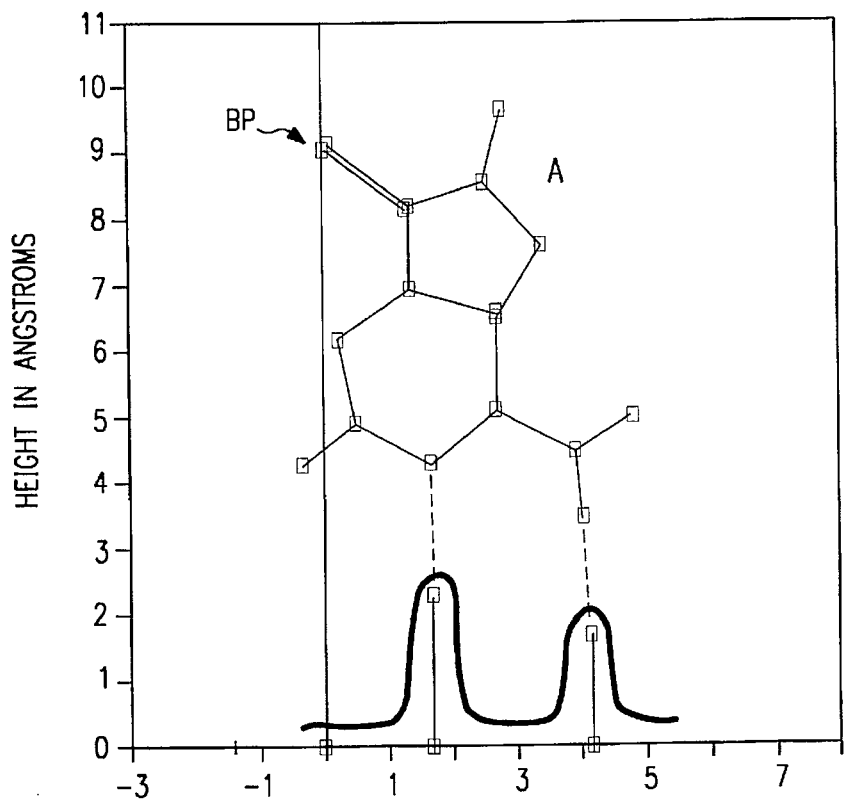
FIG. 6a depicts the proposed configuration for adenine on its template, wherein BP=chain bond points to the phosphate-sugar backbone.
Figure 6B:
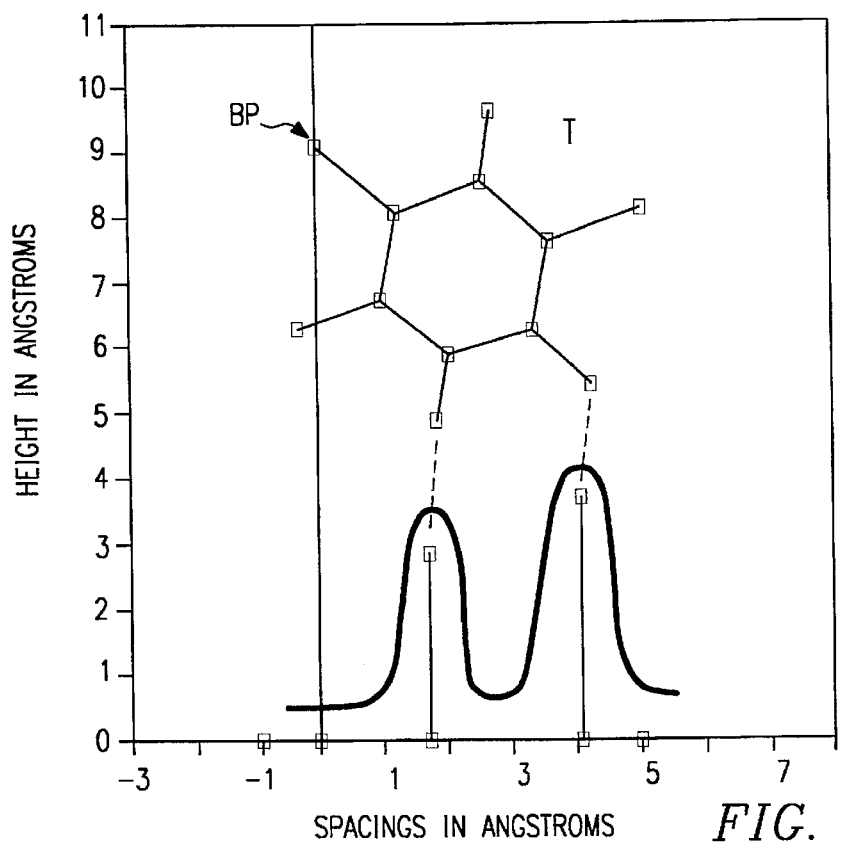
FIG. 6b depicts the proposed configuration for thymine on its template, wherein BP=chain bond points to the phosphate-sugar backbone.
Figure 6C:
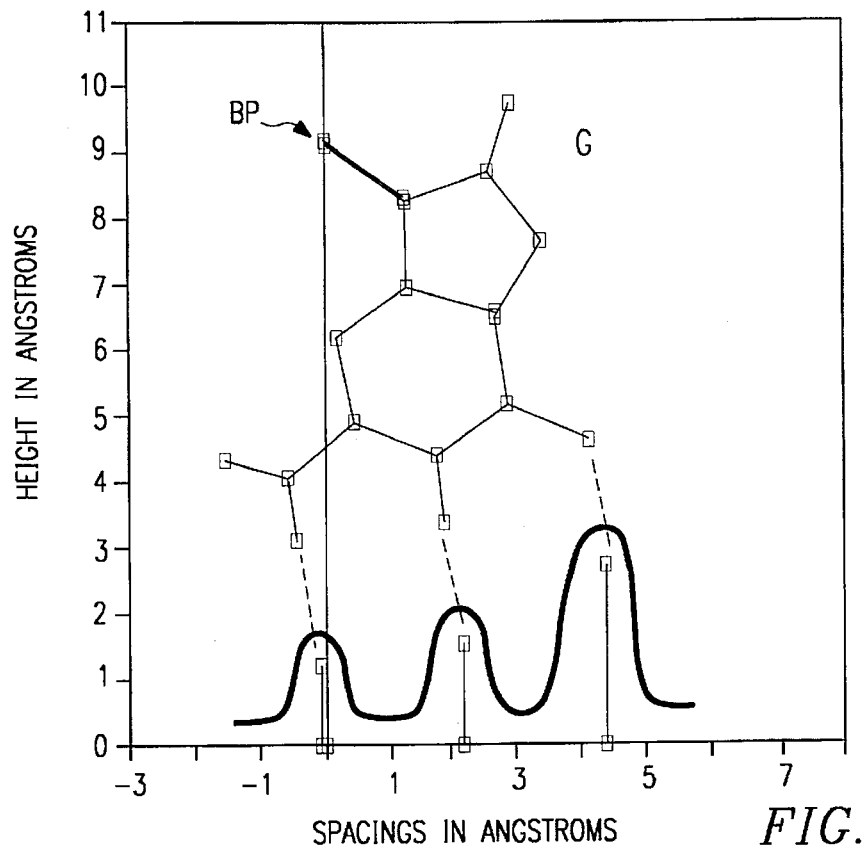
FIG. 6c depicts the proposed configuration for guanine on its template, wherein BP=chain bond points to the phosphate-sugar backbone.
Figure 6D:
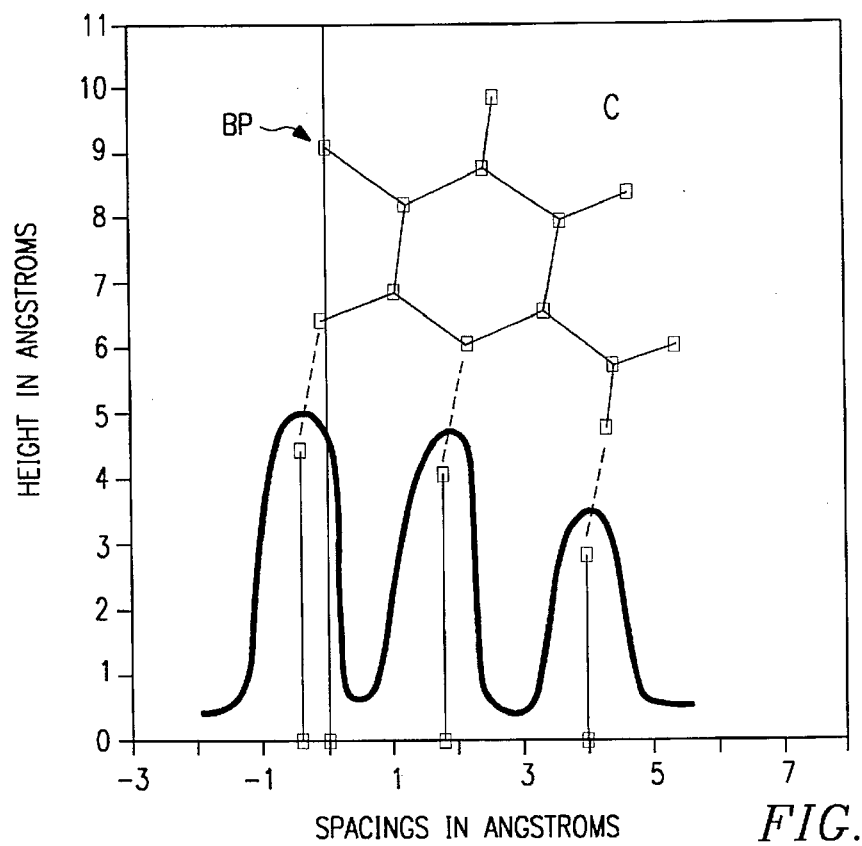
FIG. 6d depicts the proposed configuration for cytosine on its template, wherein BP=chain bond points to the phosphate-sugar backbone.

FIG. 6a depicts the dimensions of the template for adenins based upon the data listed in Table I for a 9.1 Å phosphate-sugar chain bond-point height and provides a representation of the hydrogen bonding of adenins to the template. The actual hillock heights may vary from those provided, but the distance from the top of the hillocks to the phosphate-sugar bond-point may not vary substantially. The hillock heights depicted correspond to a 9.1 Å height of the chain above the template surface plane. In the completed template, there would be no markings for the centerline of the phosphate-sugar chain—there would only be the hillock structures with their appropriate heights and spacings for the particular nucleotide sequence. FIGS. 6b, c, and d depict the positioning of thymine, guanine, and cytosine, respectively, on their template hillock structures for a common bond-point (BP) to the phosphate-sugar chain.

Figure 7:
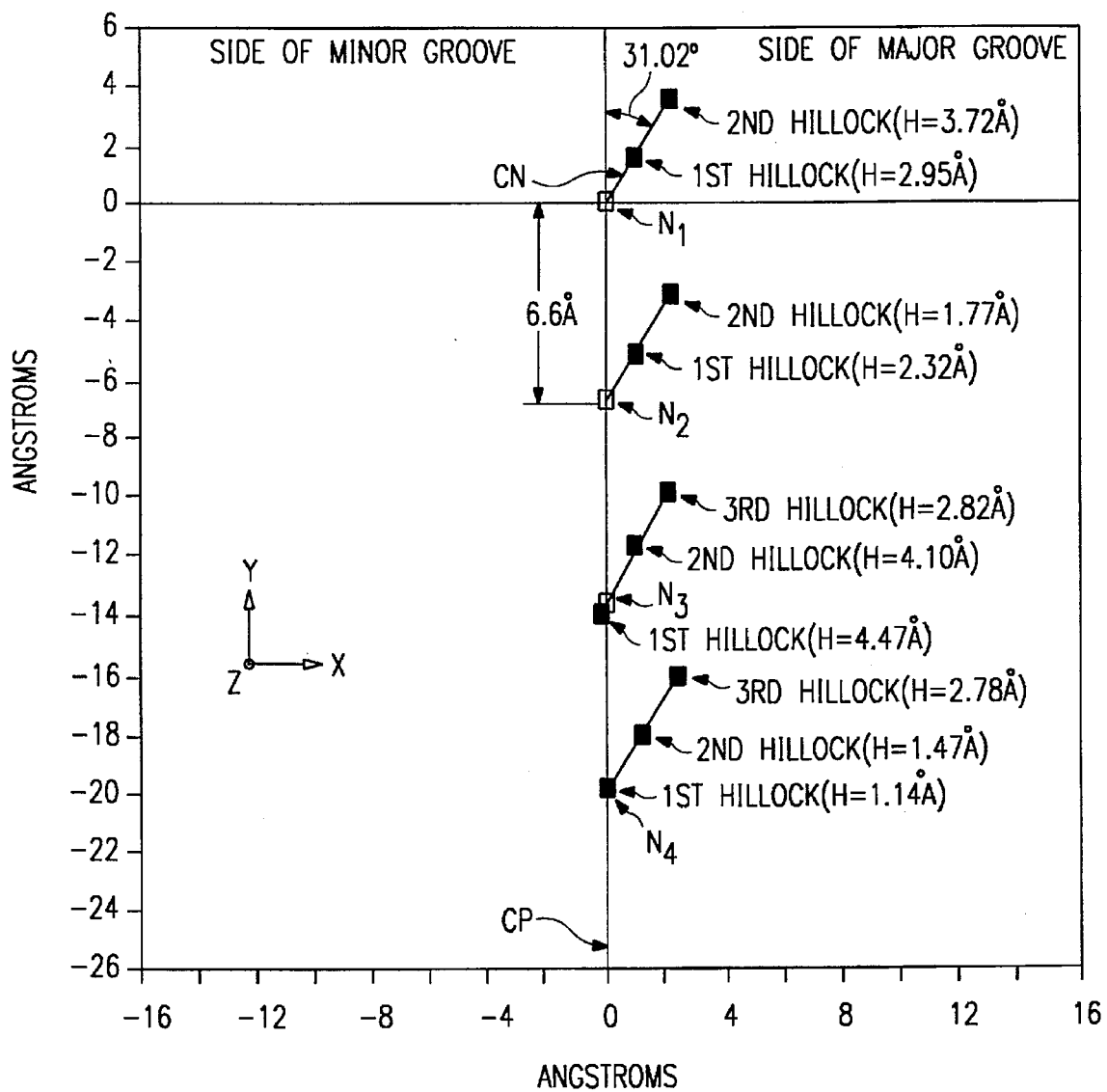
FIG. 7 depicts a top view of the proposed placement of hillocks for a simple template that would incorporate each of the four nucleotides, wherein H=template height, CN=the centerline of the nucleotide templates, CP=the centerline of the phosphate-sugar backbone located 9.1 Å above the template plane, and $N_1$, $N_2$, $N_3$ and $N_4$=the nucleotides thymine, adenine, cytosine and guanosine, respectively.

FIG. 7 depicts a proposed top view of a template comprising the four nucleotides. The centerline of the phosphate-sugar backbone is depicted on the Y axis. The starting point is the origin at coordinates (0,0).

Figure 8:
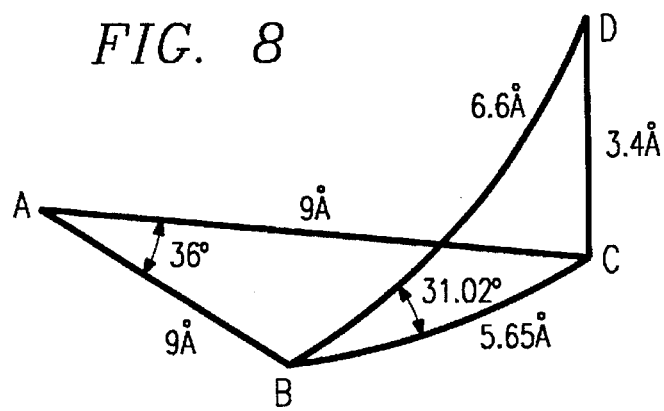
FIG. 8 depicts the chain interval length between two neighboring nucleotides in a double helix DNA molecule and the angle between the planes of the nucleotides and the phosphate sugar chain, wherein line BD=the chain interval length.

The centerline for each nucleotide is inclined at an angle of about 31° to the phosphate-sugar backbone centerline. The angle is determined by the chord length along the phosphate-sugar backbone between nucleotide bond-points, and the spacing between adjacent nucleotides which is 3.4 Å. The chord length is calculated assuming that the phosphate-sugar backbone lies on a cylinder of a radius of about 9.0 angstroms, and that the DNA molecule rotation per residue (rotation between adjacent nucleotide pairs—360° for 10 pairs) is 36°. The length of an arc subtending an angle of 36 degrees at a radius of 9.0 angstroms is 5.65Å. The chain interval is the hypotenuse of a right triangle, one side of which is the nucleotide to nucleotide spacing (3.4 Å) and the other side is the phosphate chain arc length 5.65 Å. Thus, the chain interval is about 6.60 angstroms, leading to approximately a 31° angle between the planes of the nucleotides and the phosphate-sugar backbone centerline as depicted in FIG. 8. Table II summarizes the data in FIG. 8.

TABLE II

| | |
|---|---|
| Nucleotide to nucleotide in Angstroms: DC | 3.40 |
| Rotation per residue in degrees: < BAC | 36.00 |
| Approximate effective radius of opened-out DNA single helix in angstroms. AB = AC | 9.00 |
| Length of circumference segment: BC | 5.65 |
| Chain Interval in Angstroms: BD | 6.60 |
| Angle between nucleotide plane BAC and DNA chain BD in degrees | 31.02 |

A more precise determination of the DNA radius in an uncoiled molecule may vary these computations slightly in magnitude, without departing from the scope of the invention. Thus, the nucleotide spacing along the centerline could be slightly more or less than 6.60 Å, and the angle of the nucleotide centerline and the DNA template centerline could be slightly more or less than 31° and still be within the scope of this patent teaching. It is expected that the 3.4 Å spacing between the parallel nucleotide template centerlines will be invariant.

The centerline for the DNA template can be chosen to be a straight line, spiral, serpentine, or other suitable shape over lengths long in comparison to the individual nucleotide dimensions. Total template length is calculated as the number of nucleotide pairs times the 6.60 Å chain interval in the template. Thus, the genome template for $3.2 \times 10^9$ nucleotide pairs, arranged in a serpentine or spiral pattern having a 20 Å space between rows, would occupy an area of about $4.22 \times 10^{-5}$ cm$^2$. This is a square about 65 micrometers on a side, or a circle with a radius of about 37 micrometers. Both are within the scope of this invention.

The 20 Å spacing between adjacent rows of templates approximates the diameter of the complete double helix. A reasonable deviation of this number is contemplated. The final DNA molecule will coil itself into a much more compact three-dimensional entity which permits it to fit within the cell nucleus.

A known nucleotide sequence can be put into computer-readable form such as on magnetic tape, a CDROM, a floppy or hard disc, or other data storage means. The assembly of the corresponding DNA template can then be begun.

Table I lists the X and Y coordinates of each of the nucleotide templates, as calculated based on the 31.02° angle. Each hillock is described by three numbers x, y, z where x and y determine the position in the plane of the template and z is the height of the center of the top atom in the hillock above the plane of the template. (Recalculation of the nucleotide interval length along the phosphate-sugar backbone, should it be necessary, is within the scope of the invention.) After reading the first nucleotide type, the STM can fabricate hillocks of atoms at appropriate points and with appropriate heights according to the coordinates and heights for the nucleotide as listed in Table I. The STM then indexes 6.60 Å down the phosphate-sugar backbone centerline, reads the next nucleotide type and forms the hillocks of atoms at appropriate points and with appropriate heights according to the coordinates and heights for that nucleotide, but relative to the origin of the x,y coordinates at the new location. The STM then indexes another 6.60 Å, reads the third nucleotide type from memory, and fabricates the appropriate hillocks of atoms at appropriate points according to the dimensions as given in Table I. The index spacing could vary slightly depending upon the present and previous nucleotide without deviating from the concept presented here. (It is generally accepted that the exact structure of the DNA varies with the local composition of the nucleotide pairs.) The indexing and hillock formation proceeds until the template is completed.

EXAMPLE 3

Synthesis of DNA

After a template is prepared as described in Example 2, the template can then be used to synthesize DNA molecules. One strand of DNA can be synthesized per template. Under computer control, the STM apparatus fabricates detailed hillock structures corresponding to each nucleotide of the sequence of interest in the proper locations. The template structure is prepared in advance and, depending upon the number of nucleotide pairs and the rate of formation of each nucleotide structure, could take from one to several hundred hours to fabricate.

The template can be utilized for synthesis by applying a small drop (less than 1 milliliter) of a solution containing a mixture of the deoxyribonucleotide-5'-triphosphates (hereinafter nucleotide triphosphates) of adenine, cytosine, guanine, and thymine to the surface of the template having the hillock structures. The nucleotide triphosphates are added in concentrations sufficient to bind to all their corresponding complementary hillock structures. The precise concentrations would depend upon the sequence of the DNA being synthesized, but equimolar amounts of the four nucleotide triphosphates is anticipated to be appropriate. The deoxyribonucleotide-5'-triphosphates are available from several commercial sources. The proper nucleotide triphosphate base would be attracted to the corresponding hillock structures on the template. The configuration of the hillock structures is such that the then-bound nucleotide triphosphates would be lined up next to one another.

In this configuration, the template would enable the synthesis of a single parent chain in a strained, essentially straight line, configuration. The nucleotide triphosphates can then be polymerized together using various techniques.

Figure 14:
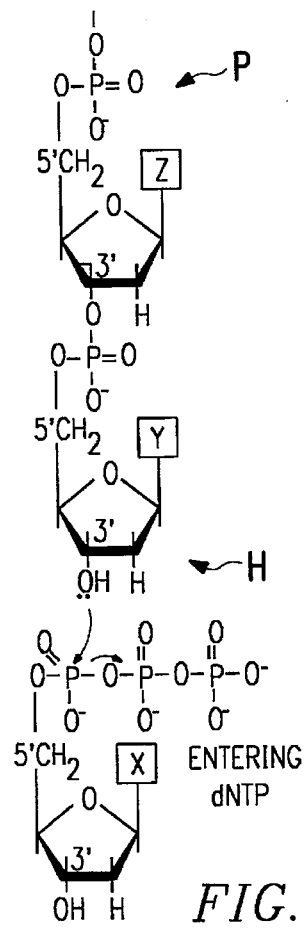
FIG. 14 depicts the reaction involved in synthesizing DNA molecules, wherein P=the phosphorylated 5' end of a growing DNA chain and H=the free 3' hydroxyl end of the growing DNA chain.

During DNA synthesis in vivo, chain formation occurs via a nucleophilic attack by the 3' hydroxyl group of the phosphate-sugar moiety of one nucleotide triphosphate upon the α-phosphorous atom of the phosphate-sugar moiety of the incoming nucleotide triphosphate. (See FIG. 14). This reaction is catalyzed in vivo by DNA Polymerase I. (Lehninger, *Biochemistry*, p. 896 (1975)). To synthesize DNA using a template of the invention, DNA Polymerase I can be added simultaneously in the solution of nucleotide triphosphates or subsequently, after a period of incubation of the nucleotide triphosphate solution on the template. (DNA Polymerase I is available commercially.)

Alternatively, once the nucleotide triphosphates have bound to their corresponding hillock structures, the entire template can be irradiated with electron beams, gamma rays, x-rays, or UV rays to effectuate polymerization. See Ogawa, Kazufumi, EP 0385656, "A Process for the Production of A Highly-Oriented Ultralong Conjugated Polymer", published Sep. 5, 1990, incorporated herein by reference. Polymerization of monomolecular films is described using 5 to 10 mJ/cm$^2$ of radiation. Additionally, the STM can be used to apply the appropriate bias voltage to the molecules to effectuate polymerization.

Figure 15:
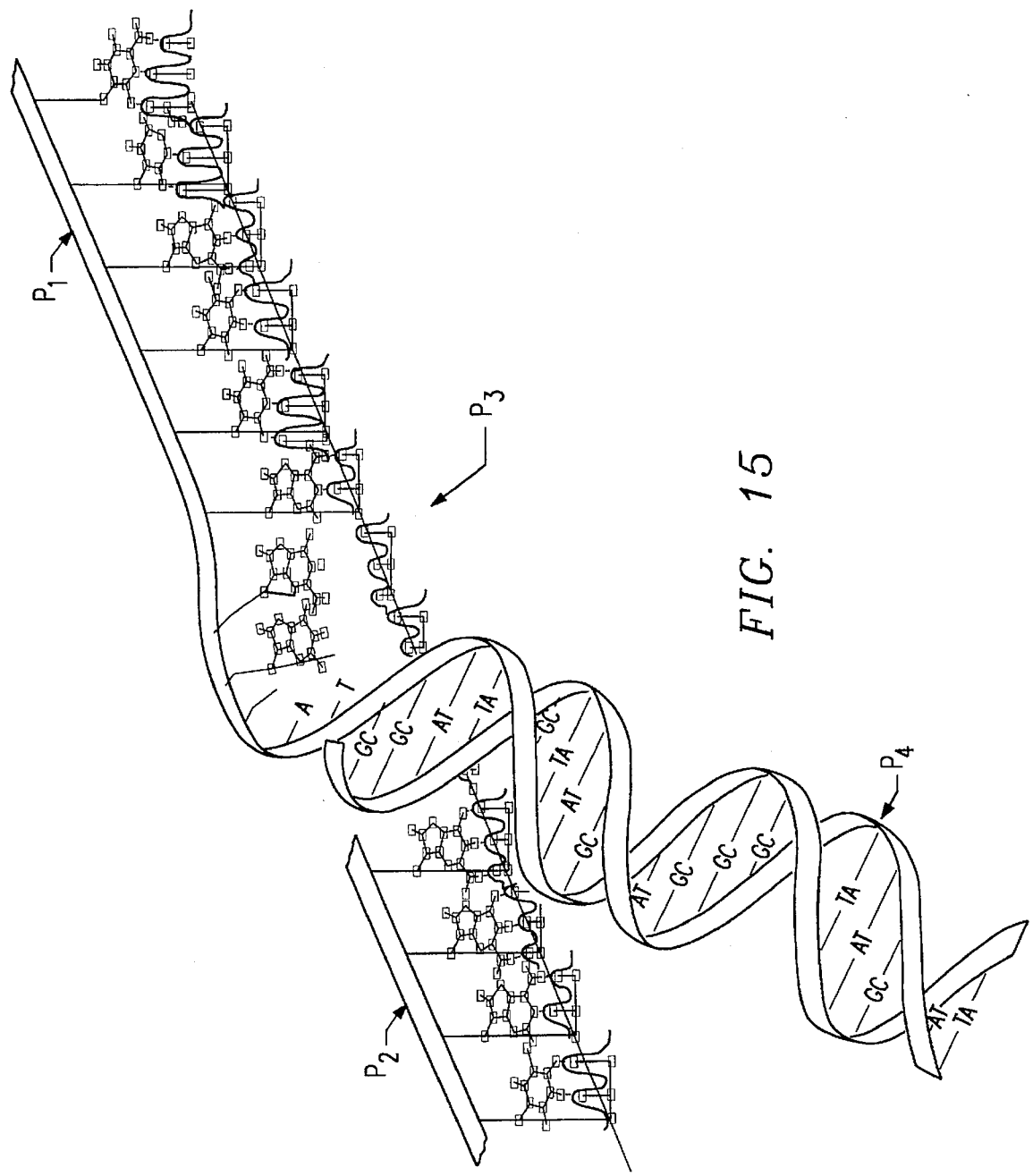
FIG. 15 represents the formation of a DNA double helix on a template of the invention and according to the method of the invention, depicting the essential features of what will actually occur in practice, wherein $P_1$=the phosphate-sugar chain of the first parent strand, $P_2$=phosphate-sugar chain of the second parent strand, $P_3$=the point of separation of the synthesized parent strand from the DNA template and $P_4$=the phosphate-sugar chain of the complementary daughter strand.

The synthesized parent strand can be released from the template by heating the template to temperatures above about 85° C. The exact temperature required depends upon the guanidine-cytosine content of the sequence. The content of these nucleotides will be determinative, since they are bound by three hydrogen bonds. (White, et al., *Principles of Biochemistry*, pp. 181–183 (1978)). As the parent strand is released from the template, internal strains at each of the bond angles will cause it to form the well-known helix. If the heating is conducted while the template is still in the presence of the solution of nucleotides, and there is an excess of nucleotide triphosphates present in the solution, a complementary daughter helix can be formed on the parent strand released from the template upon cooling of the solution, and a second parent strand can be simultaneously formed on the template itself. Polymerization of the complementary nucleotide triphosphates bound to the previously synthesized daughter strand of DNA can be effected through the use of Polymerase I, the irradiation techniques discussed above, or through use of the STM. (See FIG. 15).

Alternatively, both complementary strands of a single DNA molecule can be synthesized simultaneously on closely-spaced neighboring template structures. The sequential heating and cooling of the template solutions, followed by combination of the solutions, will enable the release of the complementary strands from their respective templates and their subsequent binding to one another upon cooling to form a complete double helix.

Figure 9:
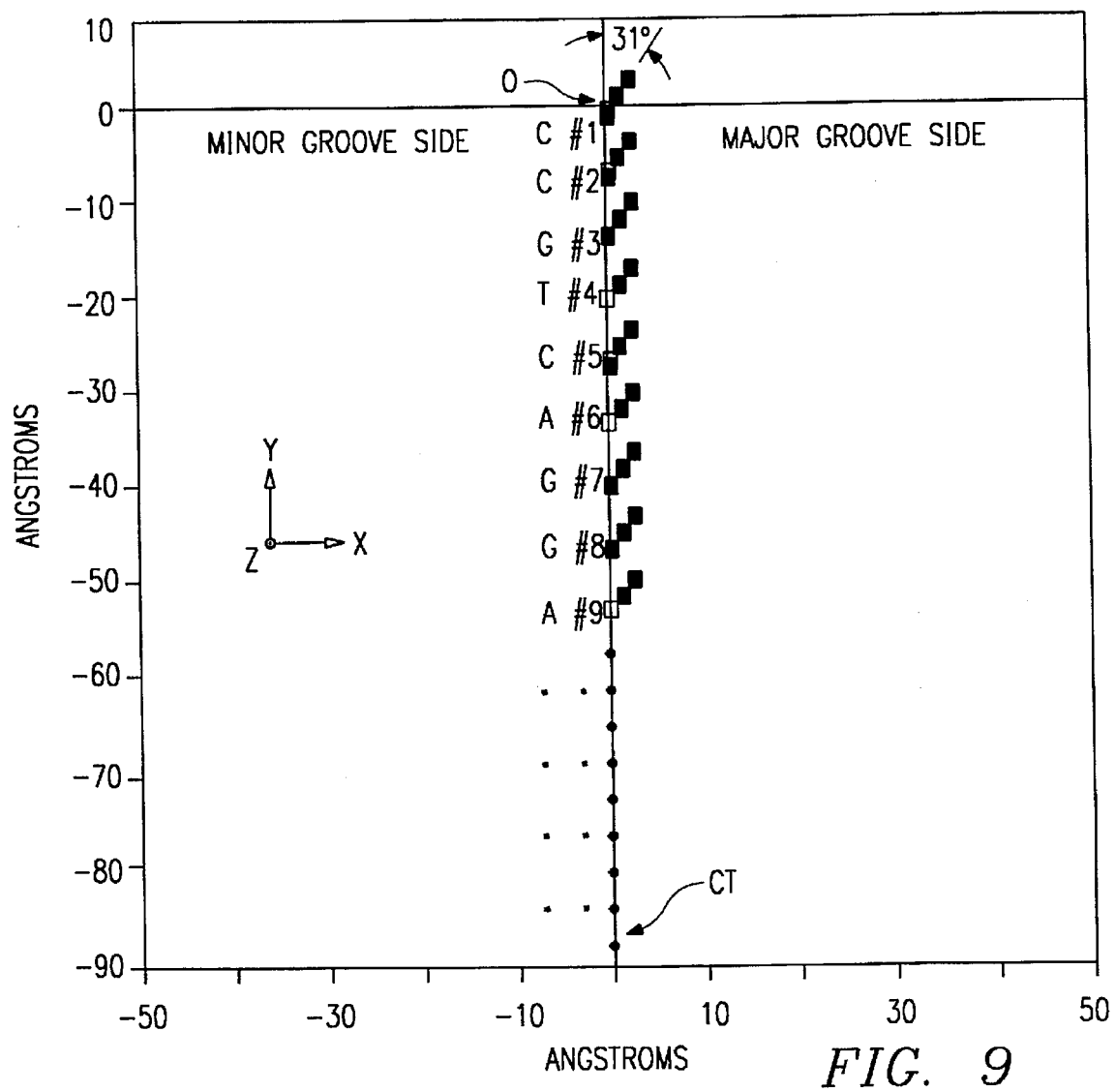
FIG. 9 is a top view depicting the locations of the hillocks for the template for the first nine nucleotides of the $\phi\chi 174$ genome, wherein O=the origin and CT=the template centerline on which another nucleotide template appears every 6.60Å.

FIG. 9 is a computer drawn proposed top view of the template hillocks of the first nine nucleotides of the reported genetic sequence for the microorganism φχ174.

Figure 10:
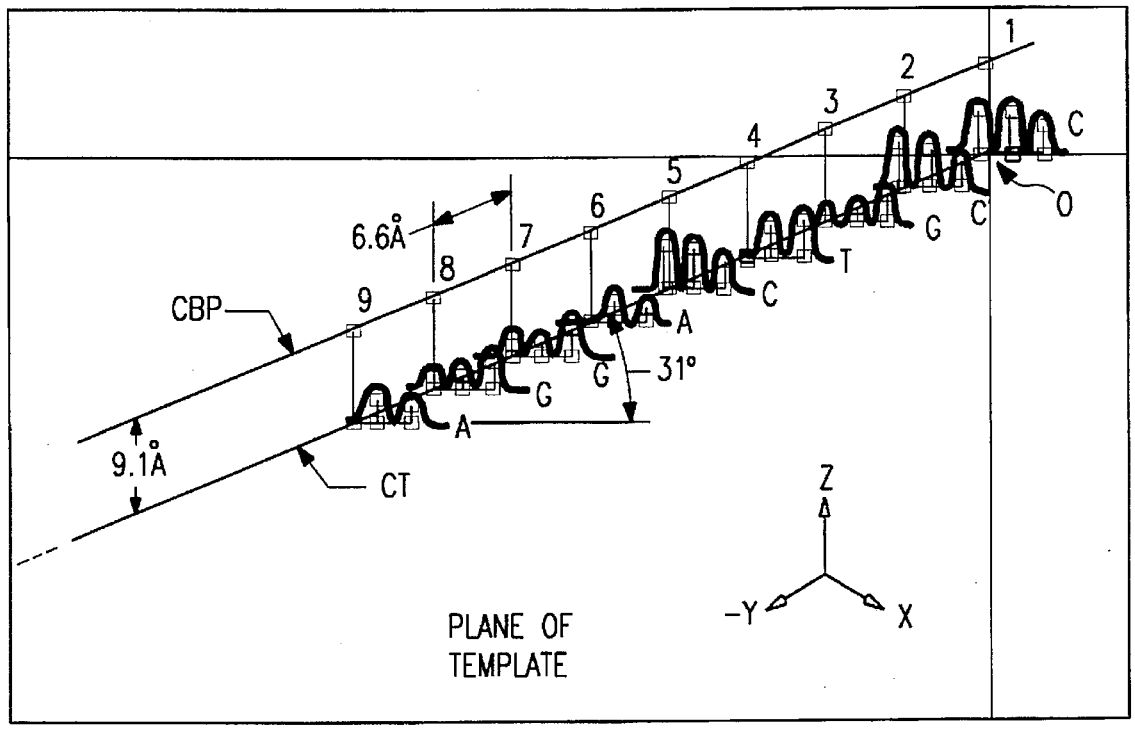
FIG. 10 is an isometric view of the first nine nucleotide template hillocks of the $\phi\chi 174$ genome showing the relative locations of the phosphate-sugar backbone bonds, wherein O=the origin, CT=the template centerline on which another nucleotide template appears every 6.60Å and CBP=the chain bond point centerline located 9.1 Å above the template plane.

FIG. 10 is an isometric visualization of the hillock structures of the first nine nucleotide base pairs for the φχ174 genome. (Phage sequence obtained from Francisco J. Ayala and John A. Kiger, Jr., *Modern Genetics*, Benjamin/Cummings Publishing Co., Inc., pp. 193–201, 1980) This figure shows the position of the bond-points for the phosphate-sugar backbone.

Figure 11:
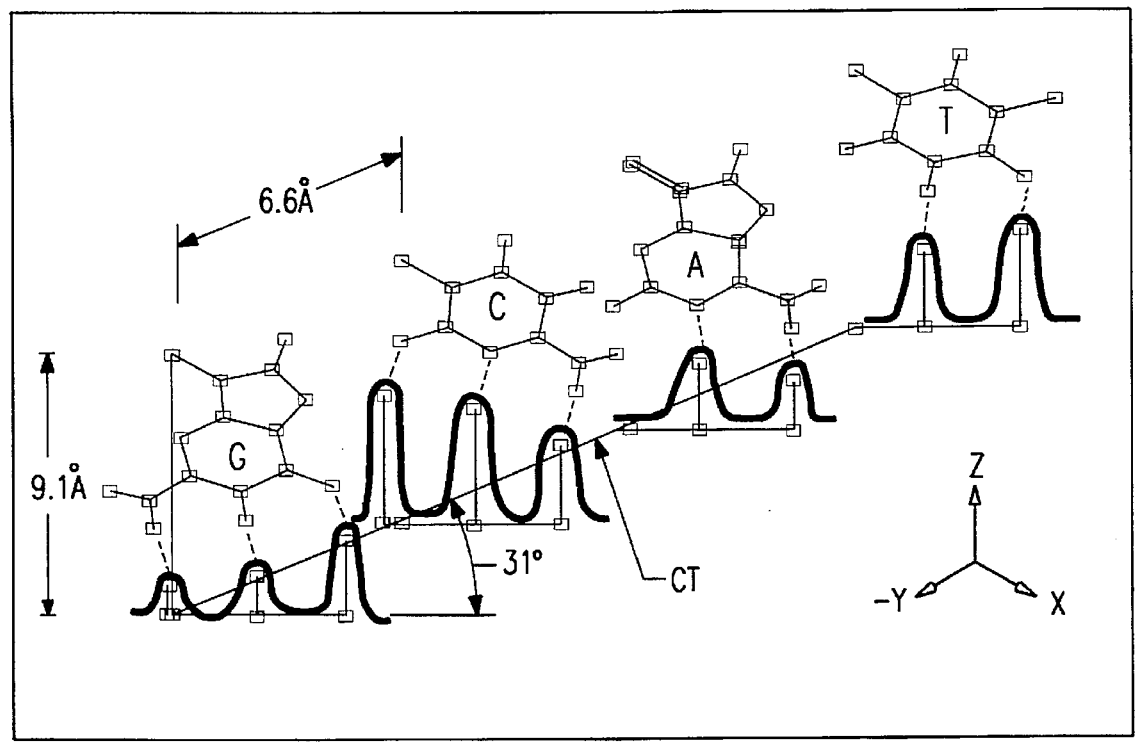
FIG. 11 is a visualization of the four nucleotides residing on their respective template hillock structures in the order depicted in FIG. 7, wherein CT=the template centerline on which another nucleotide template appears every 6.60Å.

FIG. 11 is an isometric visualization of the four distinct nucleotides residing on their respective template hillock structures. The bond-points of each nucleotide to the phosphate-sugar backbone is shown. In this drawing, the first template (thymine) is located at the origin of the complete sequence template (coordinates 0,0). The isometric drawing is done from a viewpoint 45° above the plane of the template, resulting in some foreshortening of the nucleotide images.

Figure 12:
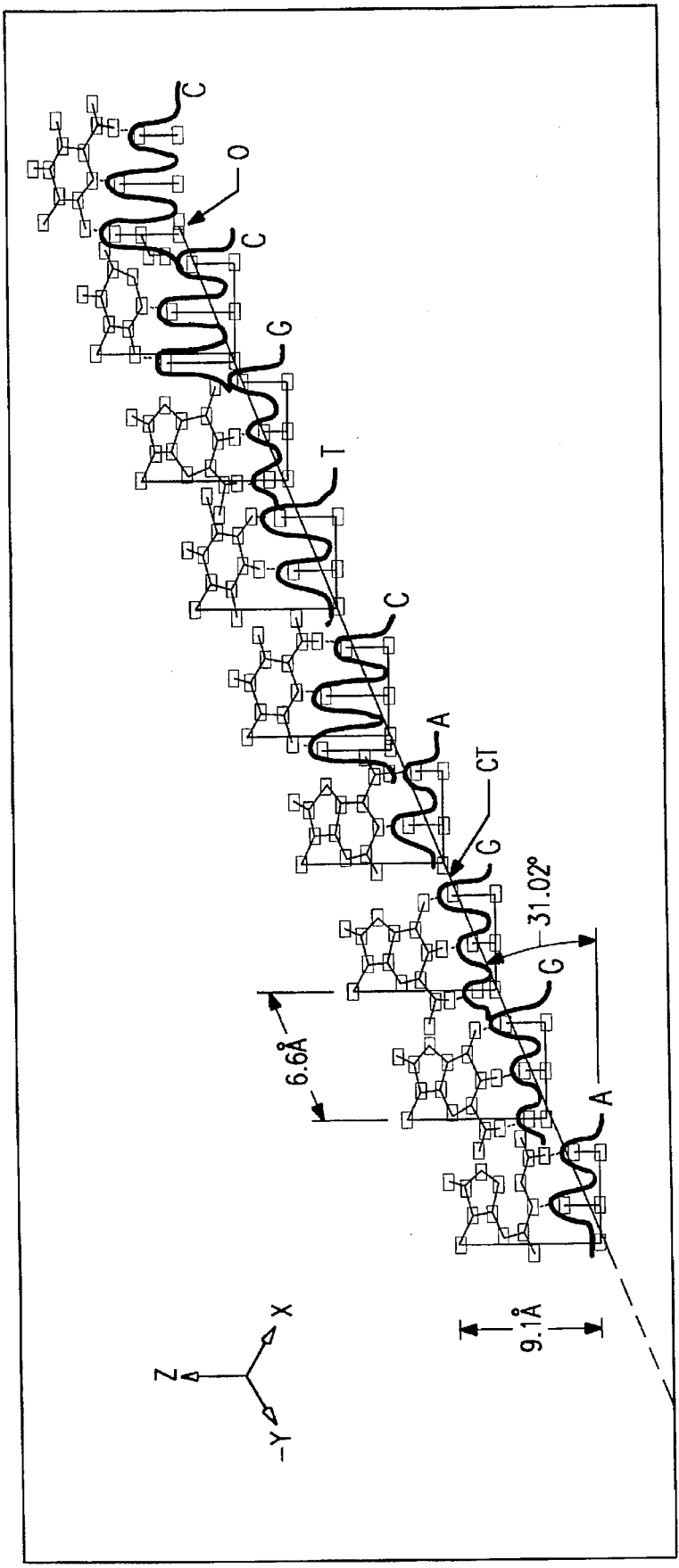
FIG. 12 is a visualization of the first nine nucleotides of the $\phi\chi 174$ genome residing on their template structures, wherein O=the origin and CT=the template centerline on which another nucleotide template appears every 6.60Å.

FIG. 12 is an isometric visualization of the first nine nucleotides of φχ174 residing on the template. As in FIG. 11, the isometric drawing is done from a viewpoint 45° above the plane of the template, resulting in some foreshortening of the nucleotide images.

Figure 13C:
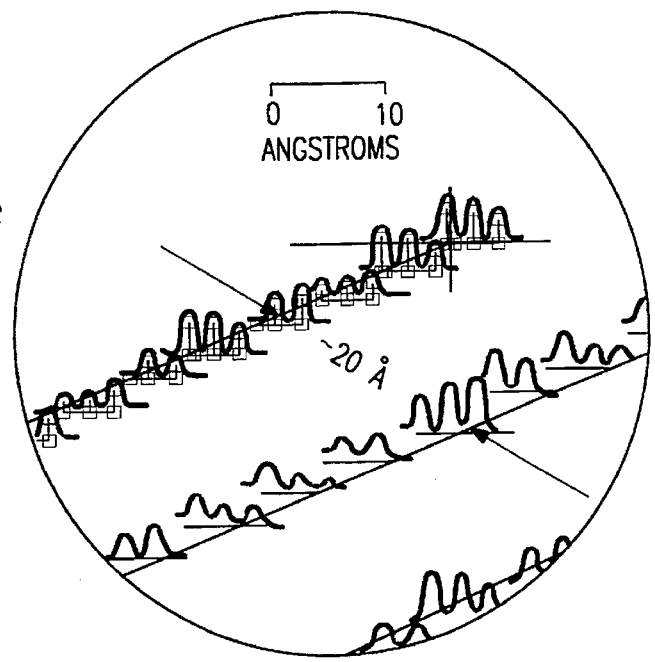
FIG. 13c is a further expanded view of region $X_2$ of FIG. 13b of the starting end of the active area of the template, depicted at approximately $1.8 \times 10^7$ times the actual dimensions.
Figure 13B:
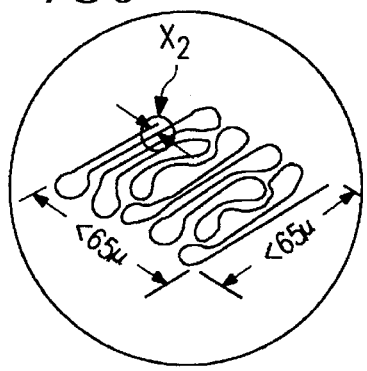
FIG. 13b is an expanded view of region $X_1$ of FIG. 13a of the template active region depicted at approximately 350 times the actual dimensions. The hillock structures are depicted in a serpentine pattern.
Figure 13A:
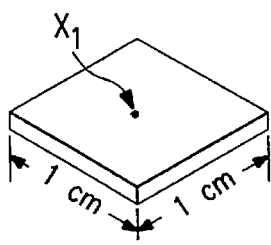
FIG. 13a is an overall view of the proposed template depicted at approximately two times the actual dimensions.

FIGS. 13a, 13b and 13c depict proposed, expanded views of the template. In this drawing, the linear planar template is arranged in a modified serpentine pattern so that the entire genome length (which can be several meters long) occupies a small area on the template. The spacing between rows of templates is nominally 20 Å. The radius of curvature of the template should be much greater than 20Å, so some modification of the template spacing is required where the template must switch back on itself. One such arrangement is shown in FIG. 13b. Alternatively, a simple spiral arrangement can be utilized. Multiple templates, nested or closely spaced, can be used for the simultaneous formation of more than one DNA molecule, each with its own unique nucleotide sequence.

Fabrication of the template itself can take as long as 100 hours. However, once a template is formed, the actual, repeatable synthesis of the DNA molecule will take only a few seconds or minutes.

EXAMPLE 4

Template for Synthesis of RNA

A template for the synthesis of RNA can be prepared in a manner similar to that disclosed in Example 2. Hillocks capable of binding to the nucleotide uridine would be substituted for those binding thymidine. Since both uridine and thymidine bind to adenine, the hillocks developed for binding to thymidine will also be effective for binding uridine. Since RNA does not generally occur as a double-stranded helix, the angle for positioning the hillocks can be altered accordingly.

EXAMPLE 5

Synthesis of RNA

A template prepared as described in Example 4 can be used to synthesize RNA molecules in a similar fashion to the procedure disclosed in Example 3. The ribonucleotide-5'-triphosphates are substituted for the deoxyribonucleotide-5'-triphosphates. Furthermore, as discussed in Example 4, uridine is substituted for thymidine. Polymerization of a desired RNA molecule is effected in a manner similar to that disclosed in Example 3.

EXAMPLE 6

Synthesis of Complementary Molecules

Alternatively, the templates can be used to synthesize molecules which, while effective for complementary binding techniques, may not be appropriate for gene therapy due to the absence of the phosphate and/or sugar moieties. Instead of adding a solution of the ribonucleotide or deoxyribonucleotide triphosphates to the appropriate templates for synthesizing RNA or DNA, respectively, the ribonucleotides, deoxyribonucleotides, or the individual nucleotides themselves can be added to the template. Polymerization can be effected as disclosed in Example 3 above, using irradiation techniques or by applying the appropriate bias voltage to effect polymerization using the STM.

It will be understood that the above description is of a preferred exemplary embodiment of the invention and is intended to be illustrative of the invention, but is not to be construed to limit the scope of the invention in any way. Modifications may be made in the structural features of the invention without departing from the scope of the invention. It will be readily apparent to those skilled in the art that alternative materials may be utilized without departing from the scope of the invention.

I claim:

1. A template for selectively binding DNA or RNA molecules comprising:

a) a substrate having an essentially flat surface;

b) a multiplicity of hillocks, said hillocks comprising at least one atom specifically positioned on said surface to form a three-dimensional pattern, said pattern dimensioned to facilitate binding between clusters of said hillocks and regions on DNA or RNA molecules complementary to said hillock clusters wherein said binding is by hydrogen bonding.

2. A template according to claim 1 wherein said hillocks are comprised of at least one atom which is a halogen.

3. A template according to claim 1 wherein said hillocks are comprised of at least one atom selected from the group consisting of oxygen, nitrogen, chlorine and fluorine.

4. A method of separating a single stranded nucleic acid molecule of a particular sequence from a heterogenous mixture, comprising the steps of:

a) constructing a template by using a scanning tunneling microscope, said template capable of specifically binding to said single stranded nucleic acid molecule of a particular sequence; and b) exposing said template to said heterogenous mixture under conditions effective to permit binding of said particular sequence to said template to form a bound fraction and an unbound fraction;

c) separating said bound fraction from said unbound fraction whereby said single stranded nucleic acid of a particular sequence is isolated from said, heterogeneous mixture wherein said binding is by hydrogen bonding.

5. The method according to claim 4, further comprising analyzing said bound fractions to detect the presence of nucleic acids.

6. The method according to claim 5, wherein said bound fraction is removed from said template and then subjected to nucleic acid analysis.

7. The method according to claim 5, wherein said bound fraction is analyzed on said template.

* * * * *